(12) United States Patent
Nijman et al.

(10) Patent No.: US 9,439,786 B2
(45) Date of Patent: Sep. 13, 2016

(54) PROSTHETIC ANKLE MODULE

(71) Applicant: Ossur hf, Reykjavik (IS)

(72) Inventors: Jeroen Nijman, Reykjavik (IS); Christophe Lecomte, Reykjavik (IS); Grimur Jonsson, Vogar (IS)

(73) Assignee: Össur hf, Reykjavik (IS)

( * ) Notice: Subject to any disclaimer, the term of this patent is extended or adjusted under 35 U.S.C. 154(b) by 0 days.

(21) Appl. No.: 13/955,988

(22) Filed: Jul. 31, 2013

(65) Prior Publication Data

US 2014/0039642 A1  Feb. 6, 2014

Related U.S. Application Data

(60) Provisional application No. 61/678,493, filed on Aug. 1, 2012.

(51) Int. Cl.
*A61F 2/66* (2006.01)
*A61F 2/64* (2006.01)

(52) U.S. Cl.
CPC ............... *A61F 2/6607* (2013.01); *A61F 2/66* (2013.01); *A61F 2/644* (2013.01); *A61F 2002/6664* (2013.01)

(58) Field of Classification Search
CPC ....... A61F 2/66; A61F 2/6607; A61F 2/6678
See application file for complete search history.

(56) References Cited

U.S. PATENT DOCUMENTS

| 35,686 A | 6/1862 | Jewett |
| 53,931 A | 4/1866 | Weston |
| 57,666 A | 9/1866 | Bly |
| 368,580 A | 8/1887 | Frees |
| 411,377 A | 9/1889 | Fairchild |
| 809,876 A | 1/1906 | Wilkins |
| 987,893 A | 3/1911 | Lawrence |
| 1,023,247 A | 4/1912 | Frees |
| 1,779,765 A | 10/1930 | Eichhorn |
| 2,490,796 A | 12/1949 | Gettman et al. |

(Continued)

FOREIGN PATENT DOCUMENTS

| DE | 817186 | 10/1951 |
| DE | 834884 | 3/1952 |

(Continued)

OTHER PUBLICATIONS

Adamczyk, P., Collins, S., & Fuo, A., The advantages of a rolling foot in human walking, *The Journal of Experimental Biology* 209, 3953-3963 (2006).

(Continued)

*Primary Examiner* — Bruce E Snow
(74) *Attorney, Agent, or Firm* — Knobbe, Martens, Olson & Bear, LLP

(57) ABSTRACT

A prosthetic ankle module allows for translational and/or rotational movement of a prosthetic foot relative to an adapter. The ankle module can include a four-bar linkage assembly. Links of the linkage assembly can be arranged in various configurations, e.g., parallel or non-parallel and having equal or non-equal lengths, to provide different functions and benefits, e.g., dorsiflexion, plantar flexion, vertical shock absorption, inversion, eversion, and/or rotation about the sagittal axis. Other types of linkage assemblies are also possible. A prosthetic foot can further include a support spring to limit the range of motion of the adapter in use.

11 Claims, 35 Drawing Sheets

(56) References Cited

U.S. PATENT DOCUMENTS

| | | |
|---|---|---|
| 2,529,968 A | 11/1950 | Sartin |
| 2,573,347 A | 10/1951 | Mazzola |
| 2,605,474 A | 8/1952 | Oliver |
| 2,619,652 A | 12/1952 | Vesper |
| 2,620,485 A | 12/1952 | Greissinger et al. |
| 2,692,392 A | 10/1954 | Bennington et al. |
| 2,731,645 A | 1/1956 | Woodall |
| 2,851,694 A | 9/1958 | Valenti |
| 3,480,972 A | 12/1969 | Prahl et al. |
| 3,551,914 A | 1/1971 | Woodall |
| 3,784,988 A | 1/1974 | Trumpler |
| 3,823,424 A * | 7/1974 | May .................. A61F 2/644 623/39 |
| 3,874,004 A | 4/1975 | May |
| 4,145,765 A | 3/1979 | Malone |
| 4,652,266 A | 3/1987 | Truesdell |
| 5,037,444 A | 8/1991 | Phillips |
| 5,139,525 A | 8/1992 | Kristinsoon |
| 5,156,630 A | 10/1992 | Rappoport et al. |
| 5,156,632 A | 10/1992 | Wellershaus |
| 5,181,933 A | 1/1993 | Phillips |
| 5,219,365 A | 6/1993 | Sabolich |
| 5,376,133 A | 12/1994 | Gramnas |
| 5,376,141 A | 12/1994 | Phillips |
| 5,509,936 A | 4/1996 | Rappoport et al. |
| 5,549,711 A | 8/1996 | Bryant |
| 5,653,768 A | 8/1997 | Kania |
| 5,746,774 A | 5/1998 | Kramer et al. |
| 5,800,568 A | 9/1998 | Atkinson et al. |
| 5,800,570 A | 9/1998 | Collier |
| 5,897,594 A | 4/1999 | Martin et al. |
| 5,948,021 A | 9/1999 | Radcliffe |
| 6,077,301 A | 6/2000 | Pusch |
| 6,187,052 B1 | 2/2001 | Molino et al. |
| 6,241,776 B1 | 6/2001 | Christensen |
| 6,306,178 B1 | 10/2001 | Kania et al. |
| 6,350,286 B1 | 2/2002 | Atkinson et al. |
| 6,402,790 B1 | 6/2002 | Celebi |
| 6,436,149 B1 | 8/2002 | Rincoe |
| 6,443,993 B1 | 9/2002 | Koniuk |
| 6,482,236 B2 | 11/2002 | Habecker |
| 6,527,811 B1 | 3/2003 | Phillips |
| 6,562,075 B2 | 5/2003 | Townsend et al. |
| 6,596,029 B1 | 7/2003 | Gramnas |
| 6,602,295 B1 | 8/2003 | Doddroe et al. |
| 6,719,807 B2 | 4/2004 | Harris |
| 6,764,521 B2 | 7/2004 | Molino et al. |
| 6,764,522 B1 | 7/2004 | Cehn |
| 6,767,370 B1 | 7/2004 | Mosler et al. |
| 6,805,717 B2 | 10/2004 | Christensen |
| 6,855,170 B2 | 2/2005 | Gramnas |
| 6,863,695 B2 | 3/2005 | Doddroe et al. |
| 6,929,665 B2 | 8/2005 | Christensen |
| 6,942,704 B2 | 9/2005 | Sulprizio |
| 6,966,933 B2 | 11/2005 | Christensen |
| 6,991,658 B2 * | 1/2006 | Slemker .................. A61F 2/76 623/38 |
| 7,172,630 B2 | 2/2007 | Christensen |
| 7,341,603 B2 | 3/2008 | Christensen |
| 7,347,877 B2 | 3/2008 | Clausen et al. |
| 7,364,593 B2 | 4/2008 | Claudino et al. |
| 7,410,503 B2 | 8/2008 | Townsend et al. |
| 7,419,509 B2 | 9/2008 | Christensen |
| 7,431,737 B2 | 10/2008 | Ragnarsdottir et al. |
| 7,507,259 B2 | 3/2009 | Townsend et al. |
| 7,520,904 B2 | 4/2009 | Christensen |
| 7,578,852 B2 | 8/2009 | Townsend et al. |
| 7,611,543 B2 | 11/2009 | Claudino et al. |
| 7,637,959 B2 | 12/2009 | Clausen et al. |
| 7,686,848 B2 | 3/2010 | Christensen |
| 7,708,784 B2 | 5/2010 | Claudino et al. |
| 7,763,082 B1 | 7/2010 | Curtis |
| 7,819,926 B1 | 10/2010 | Longino |
| 7,824,446 B2 | 11/2010 | Boren et al. |
| 7,846,213 B2 | 12/2010 | Lecomte et al. |
| 7,862,621 B2 | 1/2011 | Grab et al. |
| 7,954,502 B2 | 6/2011 | Claudino et al. |
| 7,955,399 B2 | 6/2011 | Claudino et al. |
| 7,963,998 B2 | 6/2011 | Boiten |
| 7,985,264 B2 | 7/2011 | Cheng et al. |
| 8,574,314 B2 | 11/2013 | Townsend et al. |
| 2002/0087216 A1 | 7/2002 | Adelson et al. |
| 2002/0143406 A1 | 10/2002 | Townsend et al. |
| 2003/0144745 A1 | 7/2003 | Phillips |
| 2004/0044417 A1 | 3/2004 | Gramnas |
| 2004/0054423 A1 | 3/2004 | Martin |
| 2004/0064195 A1 | 4/2004 | Herr |
| 2004/0068326 A1 | 4/2004 | Christensen |
| 2004/0225375 A1 | 11/2004 | Chen |
| 2004/0225376 A1 | 11/2004 | Townsend et al. |
| 2004/0236435 A1 | 11/2004 | Chen |
| 2004/0243253 A1 | 12/2004 | Cool et al. |
| 2005/0038525 A1 | 2/2005 | Doddroe et al. |
| 2005/0203640 A1 | 9/2005 | Christensen |
| 2006/0015192 A1 | 1/2006 | Clausen et al. |
| 2006/0030950 A1 | 2/2006 | Townsend et al. |
| 2006/0041321 A1 | 2/2006 | Christensen |
| 2006/0069448 A1 | 3/2006 | Yasui |
| 2006/0173555 A1 | 8/2006 | Harn et al. |
| 2006/0185703 A1 | 8/2006 | Claudino et al. |
| 2006/0212131 A1 | 9/2006 | Curtis |
| 2006/0224246 A1 | 10/2006 | Clausen et al. |
| 2006/0235544 A1 | 10/2006 | Iversen et al. |
| 2006/0249315 A1 | 11/2006 | Herr et al. |
| 2007/0043449 A1 | 2/2007 | Herr et al. |
| 2007/0100466 A1 | 5/2007 | Allert |
| 2007/0213840 A1 | 9/2007 | Townsend et al. |
| 2008/0004718 A1 | 1/2008 | Mosler |
| 2008/0140222 A1 * | 6/2008 | Gramnas .................. A61F 2/642 623/39 |
| 2008/0228287 A1 | 9/2008 | Ninomiya |
| 2008/0262635 A1 | 10/2008 | Moser et al. |
| 2008/0281436 A1 | 11/2008 | Claudino et al. |
| 2008/0306612 A1 | 12/2008 | Mosler |
| 2009/0012630 A1 | 1/2009 | Mosler et al. |
| 2009/0105845 A1 | 4/2009 | Curtis |
| 2009/0204229 A1 | 8/2009 | Mosler et al. |
| 2009/0204231 A1 | 8/2009 | Bonacini |
| 2009/0265019 A1 | 10/2009 | Christensen |
| 2009/0287315 A1 | 11/2009 | Lecomte et al. |
| 2010/0023135 A1 | 1/2010 | Rubie et al. |
| 2010/0030343 A1 | 2/2010 | Childress et al. |
| 2010/0042228 A1 | 2/2010 | Colvin et al. |
| 2010/0174385 A1 | 7/2010 | Casler et al. |
| 2010/0179668 A1 | 7/2010 | Barhart et al. |
| 2011/0071650 A1 | 3/2011 | Claudino et al. |
| 2011/0166674 A1 | 7/2011 | Montmartin |
| 2011/0295385 A1 | 12/2011 | Herr et al. |
| 2012/0016493 A1 | 1/2012 | Hansen et al. |
| 2012/0078380 A1 | 3/2012 | Jonsson et al. |
| 2013/0085581 A1 | 4/2013 | Lecomte |

FOREIGN PATENT DOCUMENTS

| | | |
|---|---|---|
| DE | 298 20 904 | 6/1999 |
| GB | 117547 | 8/1918 |
| GB | 120462 | 11/1918 |
| WO | WO 91/15171 | 10/1991 |
| WO | WO 2011/066354 | 6/2011 |

OTHER PUBLICATIONS

Alaranta, H., Lempinen, V.-M., Haavisto, E., Pohjolainen, T., & Hurri, H., Subjective benefits of energy storing prosthesis, *Prosthetics and Orthotics International* 18, 92-97 (1994).

American Prosthetic Components, Inc. DuroFlex™ product shown in brochure (2 pages) and at http://www.apcomponents.com/NonMembers/DuroFlex.asp, available more than one year before Feb. 23, 2010.

Berniker, M., & Herr, H., Powered ankle-foot prosthesis to assist level-ground and stair descent gaits, *Neural Networks* 21, 654-666 (2008).

(56) References Cited

OTHER PUBLICATIONS

Barth, D., Schumacher, L., & Thomas, S., Gait analysis and energy cost of below-knee amputees wearing six different prosthetic feet, *Journal of Prosthetics and Orthotics* 4, 63-75 (1988).

Curtze, C., Hof, A., Keeken, H., Halbertsma, J., Postema, K., & Otten, B., Comparative roll-over analysis of prosthetic feet, *Journal of Biomechanics* 42, 1746-1753 (2009).

Hafner, B., Sanders, J., Czerniecki, J., & Fergason, J., Energy storage and return prostheses: does patient perception correlate with biomechanical analysis? *Clinical Biomechanics* 17, 352-344 (2002).

Hafner, B., Sanders, J., Czerniecki, J., & Fergason, J., Transtibial energy-storage-and-return prosthetic devices: A review of energy concepts and a proposed nomenclature, *Journal of Rehabilitation Research and Development* 39, 1-11 (2002).

Hansen, A., Effects of alignment on the roll-over shapes of prosthetic feet, *Prosthetics and Orthotics International* 32, 390-402 (2008).

Hansen, A., Meier, M., Sessoms, P., & Childress, D., The effects of prosthetic foot roll-over shape arc length on the gait of trans-tibial prosthesis users, *Prosthetics and Orthotics International* 30, 286-299 (2006).

Perry, Jacquelin, MD, Gait Analysis: Normal and Pathological Function, 1992.

Semple, R., Turner, D., Helliwell, P., & Woodburn, J., Regionalised centre of pressure analysis in patients with rheumatoid arthritis, *Clinical Biomechanics* 22, 127-129 (2007).

Ventura, J., Klute, G., & Neptune, R., The effect of prosthetic ankle energy storage and return properties on muscle activity in below-knee amputee walking, *Gait & Posture* 33, 220-226 (2011).

International Search Report and Written Opinion for PCT Application No. PCT/US2011/025766 filed on Feb. 22, 2011, mailed Apr. 15, 2011.

Dec. 17, 2012 International Search Report and Written Opinion for International Application No. PCT/US12/57149 filed on Sep. 25, 2012.

Nov. 8, 2013 International Search Report and Written Opinion for PCT Application No. PCT/US2013/052750 filed Jul. 30, 2013.

Extended European Search Report in corresponding European Patent Application No. 13824951.1, dated Apr. 15, 2016, in 6 pages.

\* cited by examiner

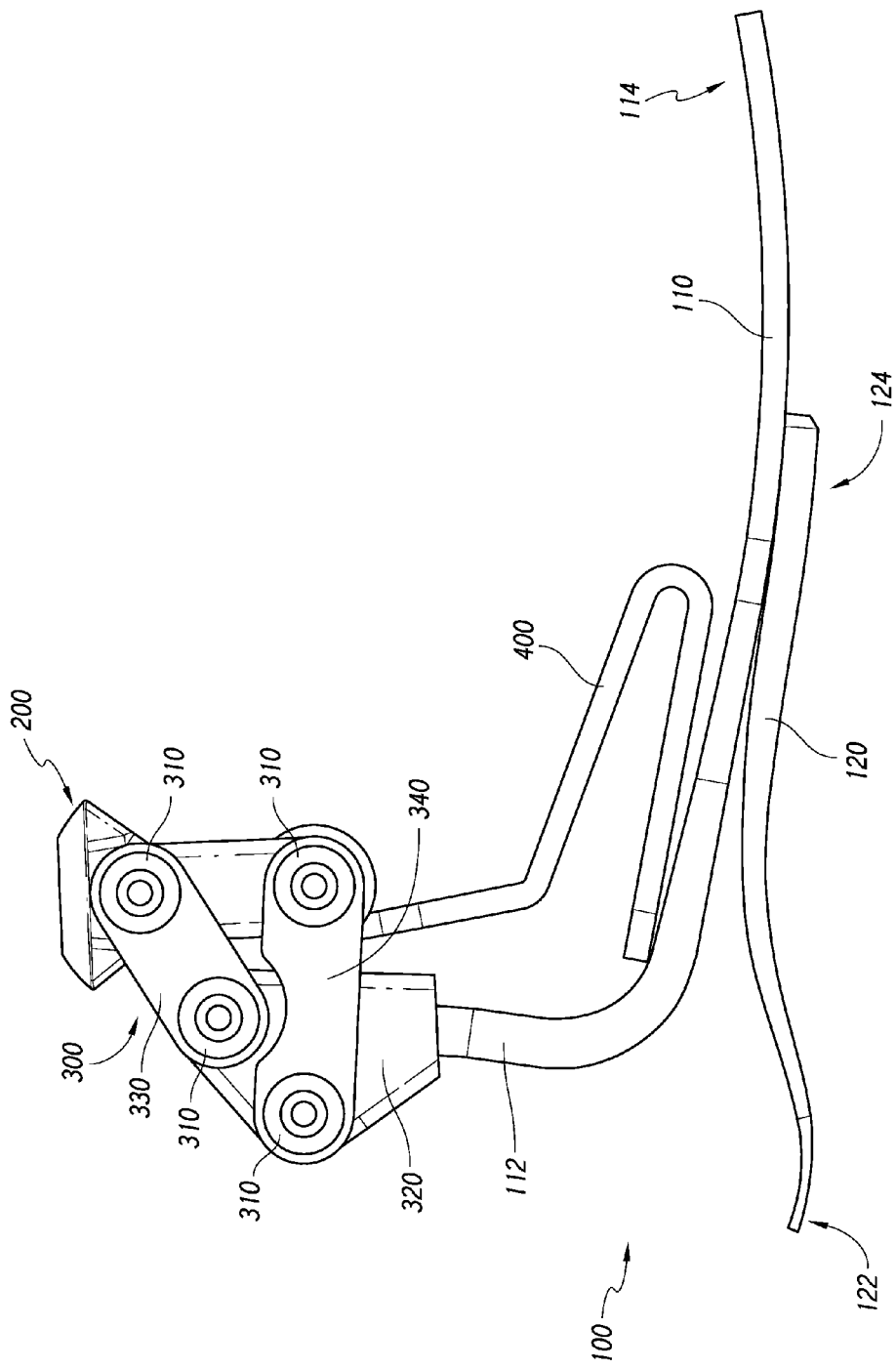

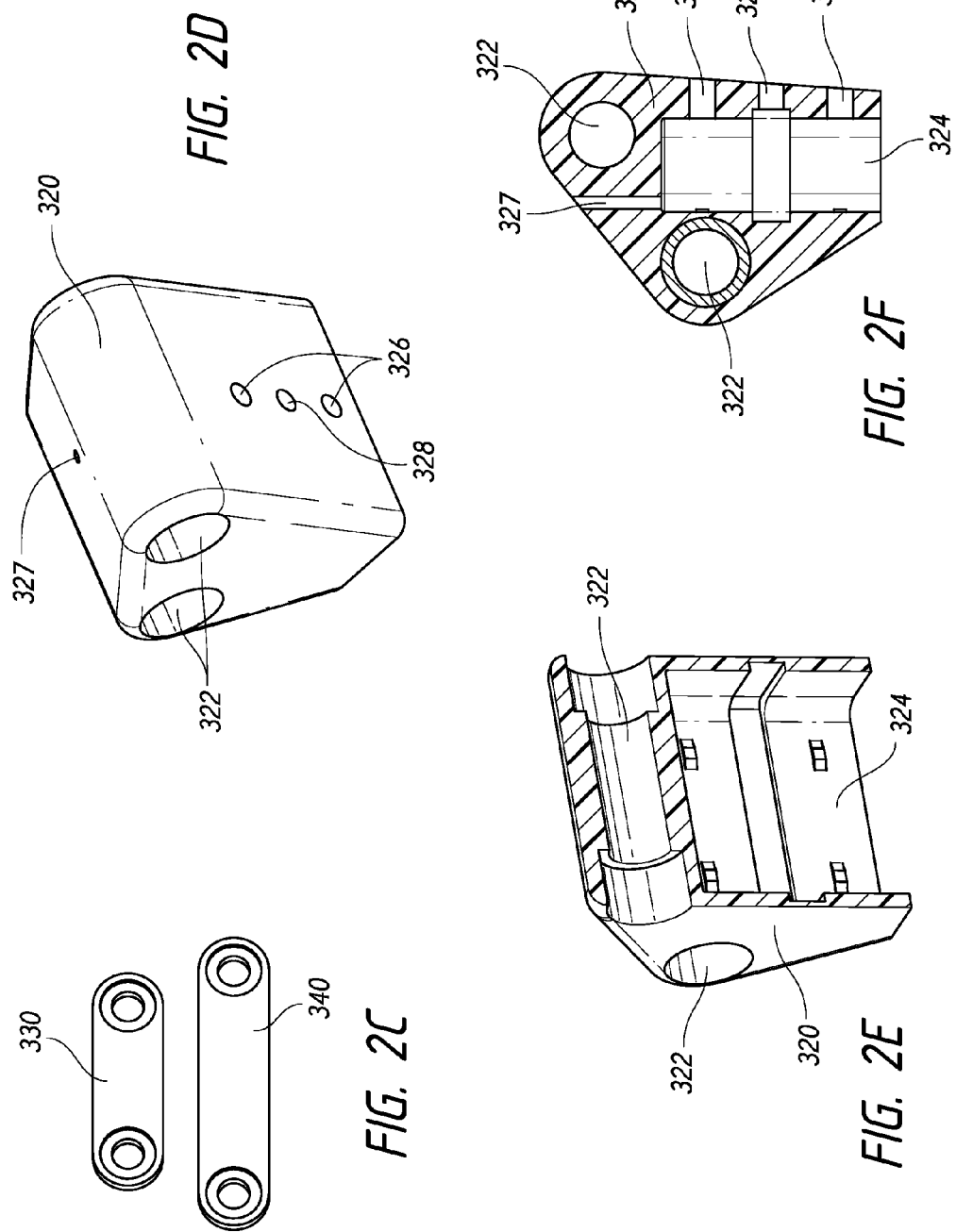

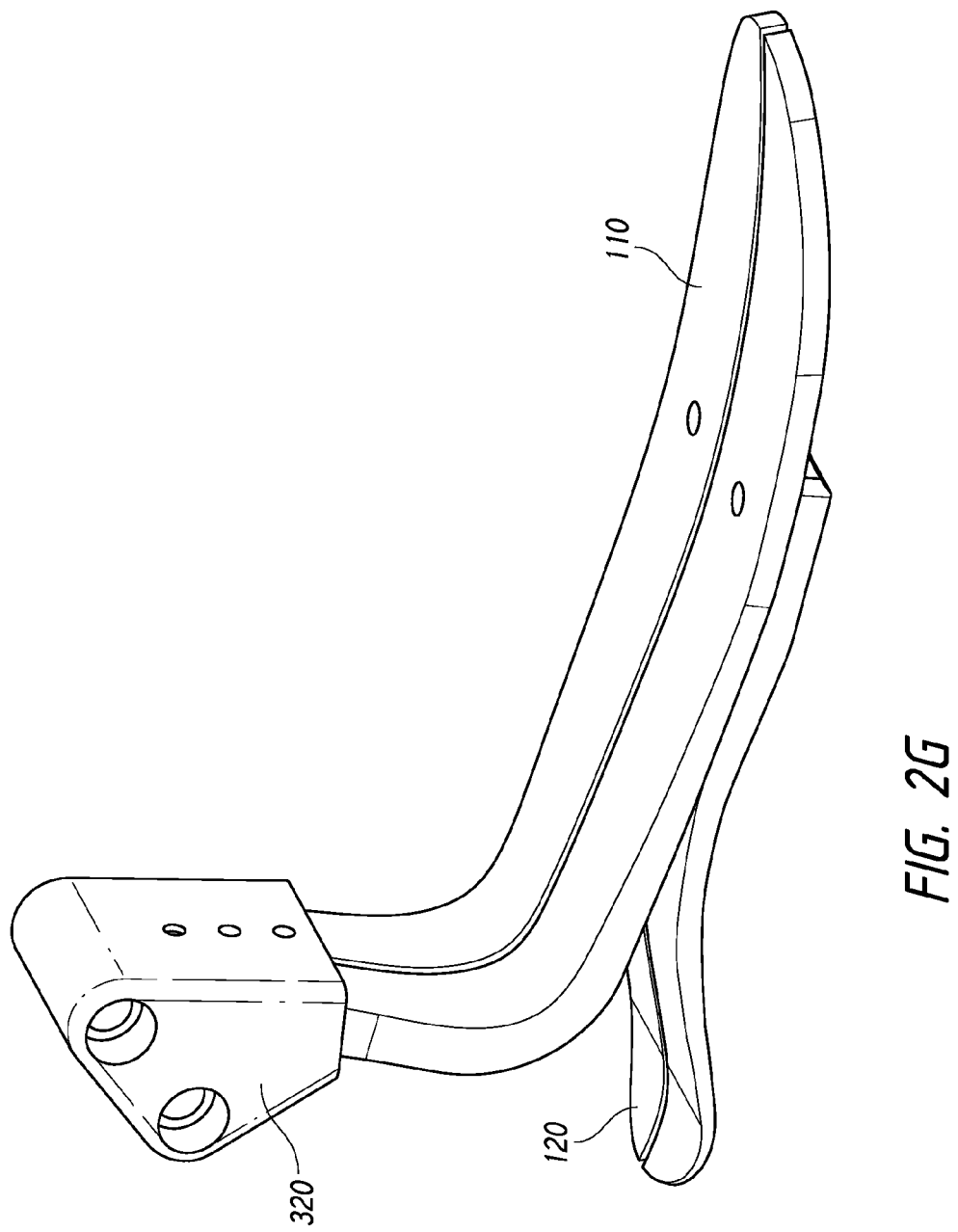

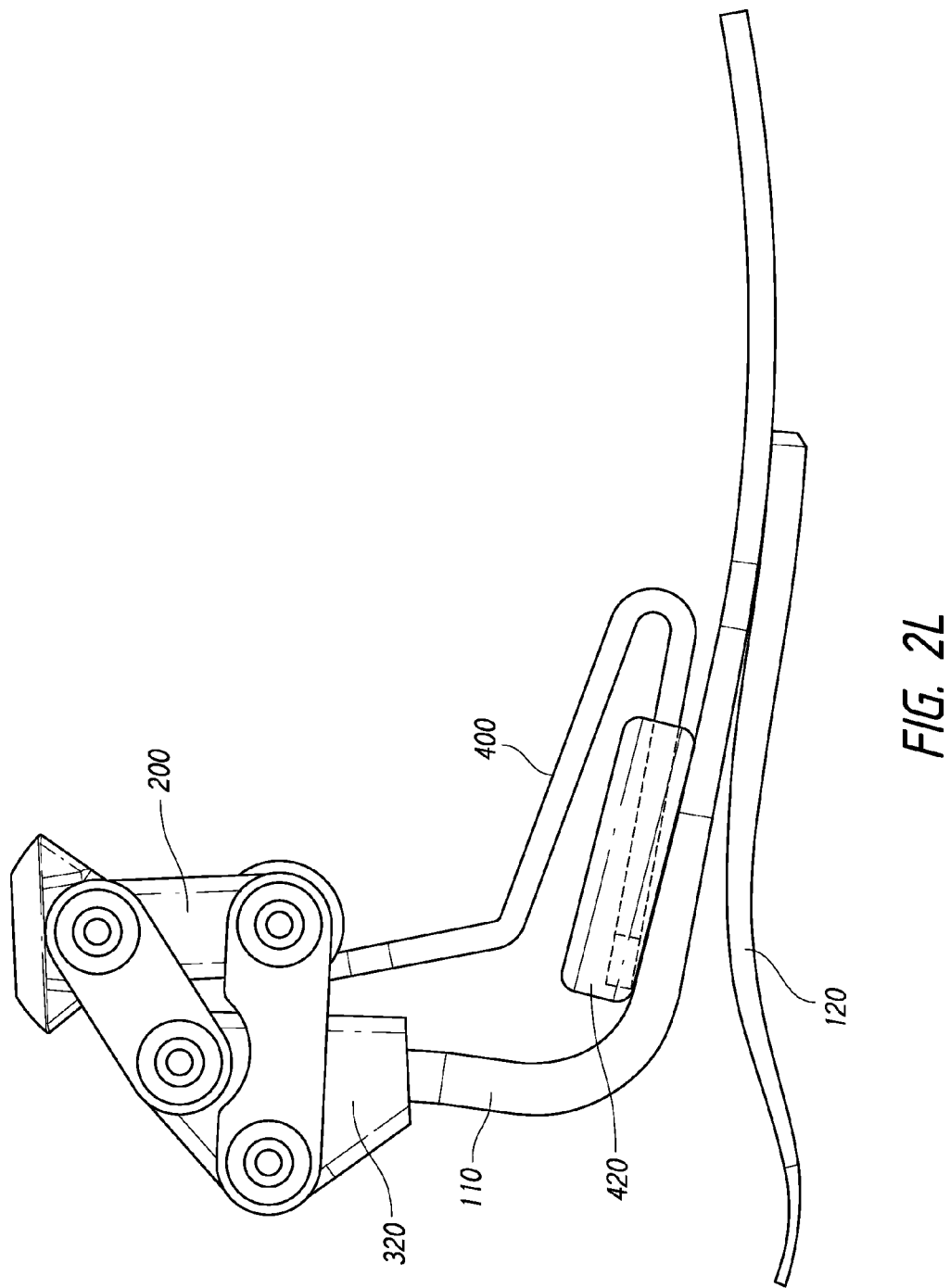

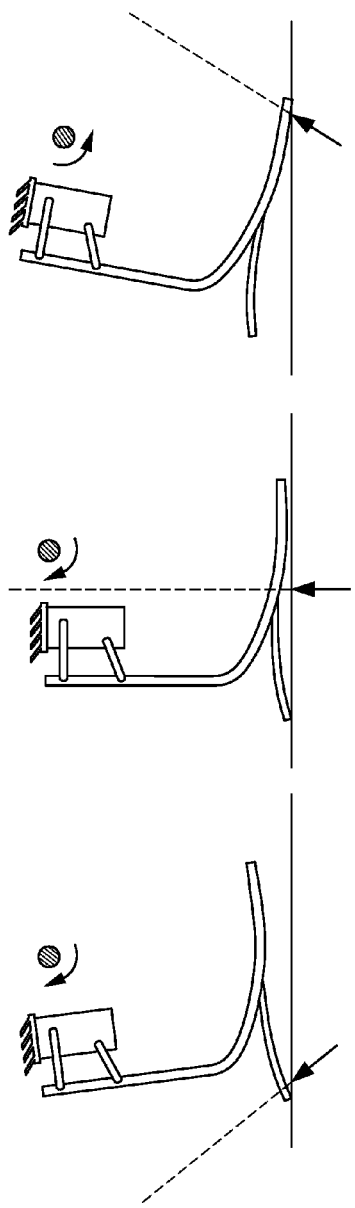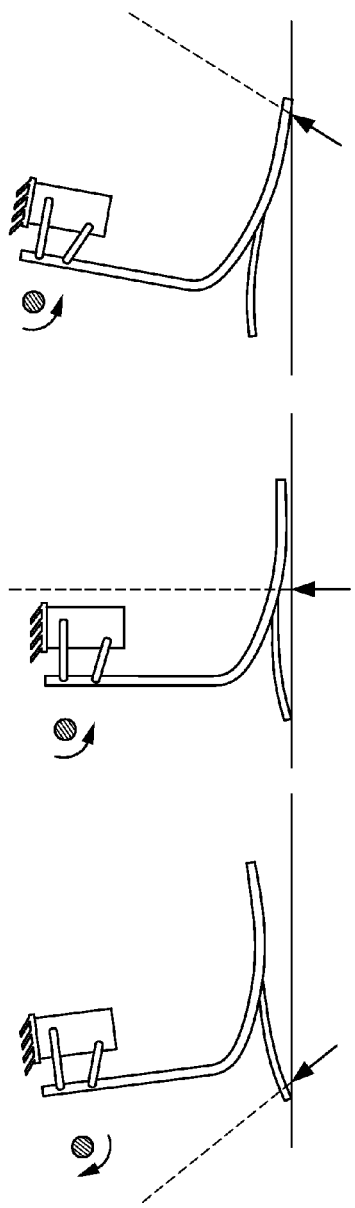
FIG. 3A  FIG. 3B  FIG. 3C
FIG. 3D  FIG. 3E  FIG. 3F

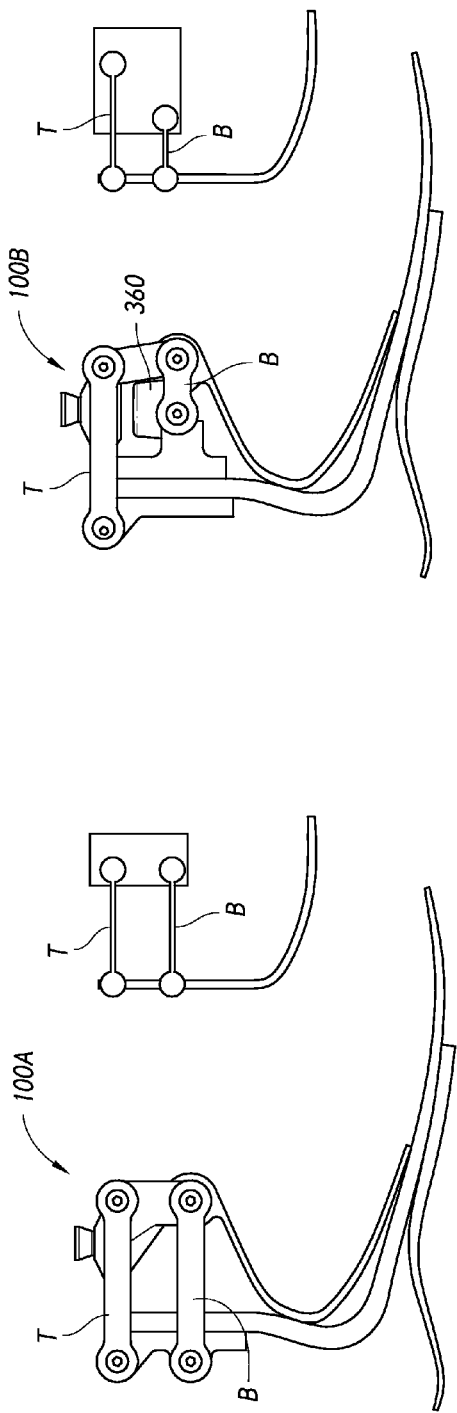
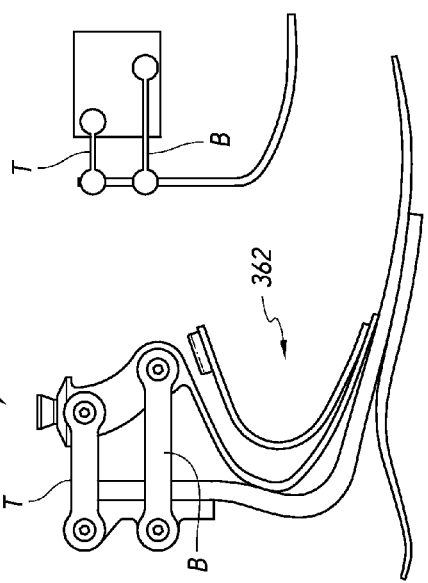
FIG. 4A  FIG. 4B  FIG. 4C

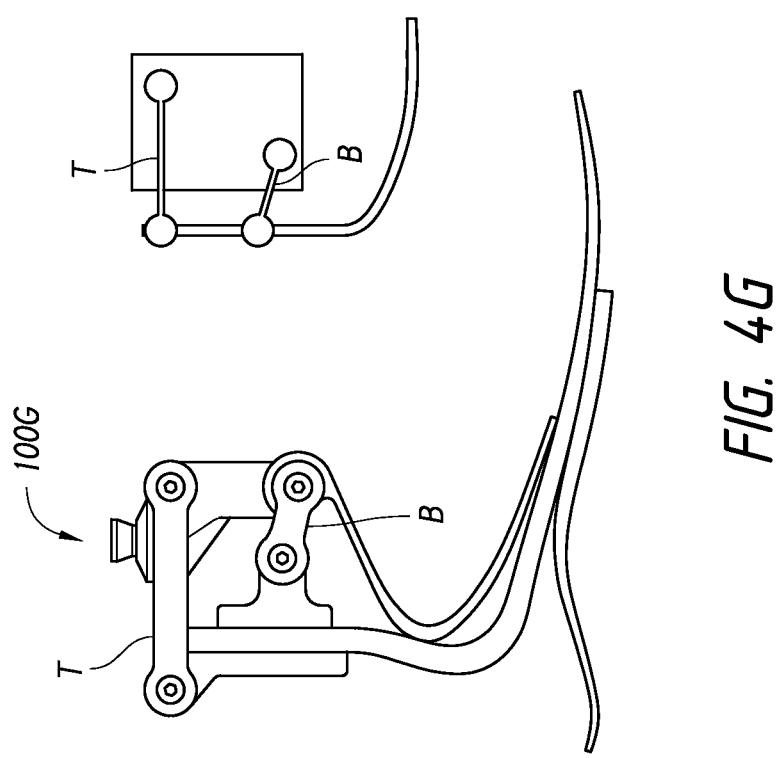

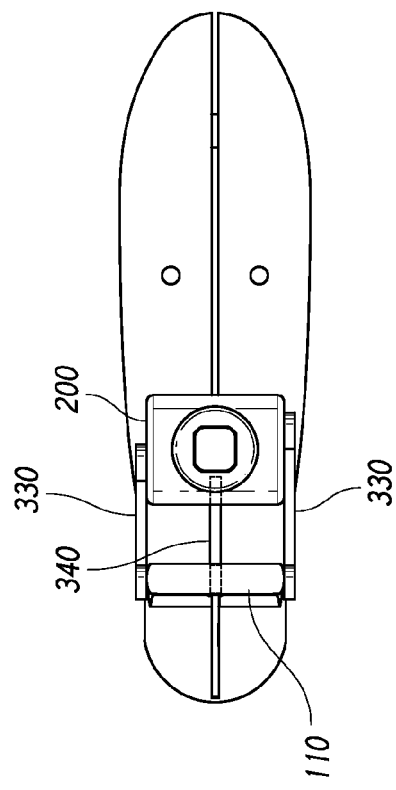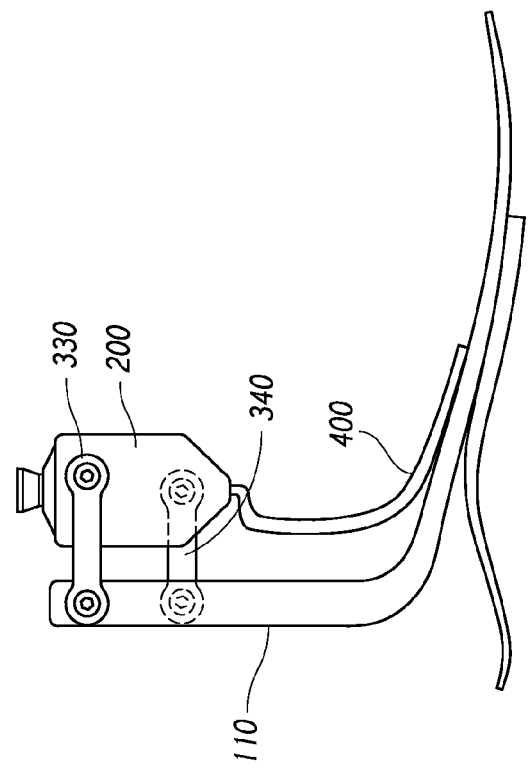
FIG. 5A
FIG. 5B

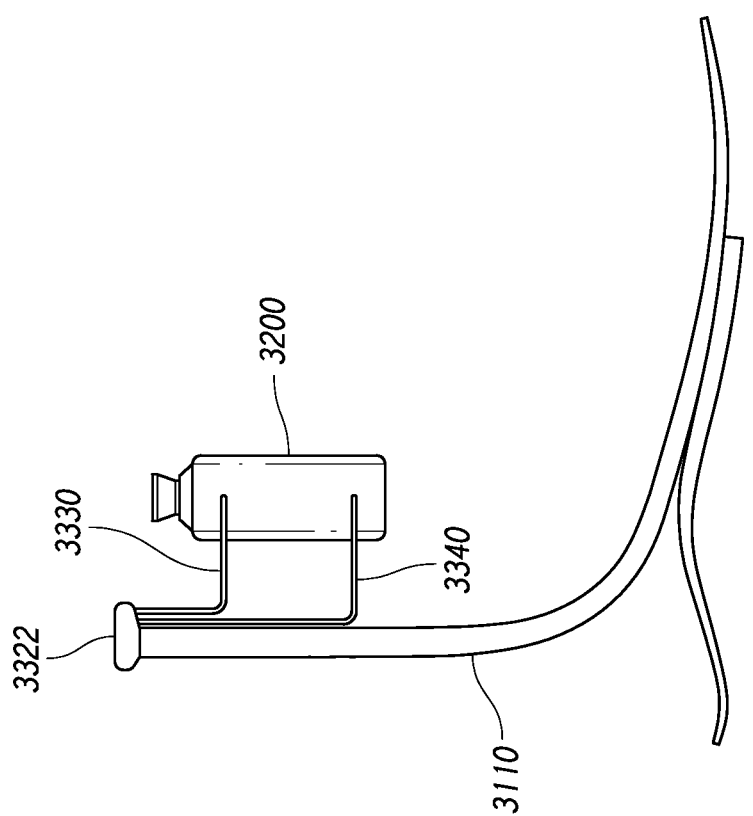

PROSTHETIC ANKLE MODULE

CROSS-REFERENCE TO RELATED APPLICATIONS

The present application claims priority benefit of U.S. Provisional Application No. 61/678,493, filed Aug. 1, 2012, the entirety of which is hereby incorporated by reference herein and should be considered a part of this specification.

BACKGROUND

1. Field

The present application relates to prosthetics in general, and more particularly, to prosthetic feet having a prosthetic ankle module and/or support spring.

2. Description of the Related Art

Various types of prosthetic devices are available as substitutes for human limbs and joints. Many prosthetic devices available today incorporate various features to try to better approximate the functioning of natural limbs and joints. For example, some prosthetic foot designs seek to provide improved foot rollover, ankle function, and energy storage and return during use.

Prosthetic feet are often attached to a user's residual limb or other prosthetic components (e.g., a pylon) via adapters that may be bolted, glued, or otherwise coupled directly to the foot. Conventional adapters can allow for relative adjustment between prosthetic components during alignment, but typically fix the components relative to each other during use.

SUMMARY

A prosthetic ankle module according to the present disclosure is configured to couple a prosthetic foot to an adapter, which in turn is configured to be coupled to a user's residual limb or another prosthetic component, such as a pylon. The ankle module allows for relative movement (i.e., translation and/or rotation) between the foot and adapter during ambulation, which results in improved rollover performance of the foot. A prosthetic foot according to the present disclosure can also include a support spring to help limit the range of motion of the adapter during use and provide additional shock absorption during ambulation.

In some embodiments, a prosthetic foot assembly includes an elongate foot member, an adapter assembly, and an ankle module. The elongate foot member has a generally vertical attachment portion at a proximal end, and the adapter assembly is configured to be coupled to another prosthetic component, such as a socket or pylon. The ankle module couples the attachment portion of the foot member to the adapter assembly via two or more joints and allows translational and/or pivotal movement of the foot member relative to the adapter assembly via the joints.

In some embodiments, a prosthetic foot assembly includes an elongate foot member, an adapter assembly, and one or more linkages. The elongate foot member has a generally vertical attachment portion at a proximal end. The adapter assembly is configured to be coupled to another prosthetic component, such as a socket or pylon. In some embodiments, the adapter assembly is horizontally spaced from the generally vertical attachment portion of the foot member. The attachment portion is configured to move relative to the adapter assembly during ambulation of the prosthetic foot. The linkages extend between and pivotally couple the vertical attachment portion and adapter assembly to allow the foot member to pivotally move relative to the adapter portion during ambulation. In some embodiments, the linkages facilitate plantarflexion of the foot upon heel strike.

In some embodiments, a prosthetic foot assembly includes an adapter assembly, an elongate foot member, and a linkage assembly. The adapter assembly is configured to be coupled to another prosthetic component, such as a socket or pylon, and includes two or more joints. A proximal end of the elongate foot member includes a generally vertical attachment portion that includes two or more joints and is horizontally spaced from the adapter assembly. The linkage assembly couples and allows relative movement between the foot member and the adapter assembly. The linkage assembly includes an upper link and a lower link on both a medial and a lateral side of the foot member and adapter assembly. The links extend between the joints of the adapter assembly and foot member. In some embodiments, the upper links have different lengths than the lower links and the upper links and lower links are not parallel.

For purposes of summarizing the disclosure and the advantages achieved over the prior art, certain objects and advantages are described herein. Of course, it is to be understood that not necessarily all such objects or advantages need to be achieved in accordance with any particular embodiment. Thus, for example, those skilled in the art will recognize that the disclosure may be embodied or carried out in a manner that achieves or optimizes one advantage or group of advantages as taught or suggested herein without necessarily achieving other objects or advantages as may be taught or suggested herein.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIG. 1A schematically illustrates an example embodiment of a foot assembly having an ankle module and support spring;

FIG. 2C schematically illustrates links of the foot assembly of FIG. 1A;

FIGS. 2D-2F schematically illustrate a connection sleeve of the foot assembly of FIG. 1A;

FIG. 2G schematically illustrates the connection sleeve of FIGS. 2D-2F coupled to a prosthetic foot;

FIG. 2L schematically illustrates the foot assembly of FIG. 1A including foam coupling the support spring to the foot;

FIGS. 3A-3F schematically illustrates hypothetical linkage assembly arrangements and the application of three different ground reaction forces to the feet;

FIGS. 4A-4I schematically illustrate example embodiments of four-bar linkage assemblies;

FIGS. 5A-6B schematically illustrate linkage assemblies allowing for three-dimensional motion;

FIGS. 8-13 schematically illustrate other embodiments of linkage assemblies;

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

A prosthetic ankle module as described herein can include one or more joints associated with a prosthetic foot and connected to one or more joints associated with an adapter. In one embodiment, the joints are pivot points that allow for rotation of one component relative to another. The joints allow the foot to move relative to the adapter during ambulation. For example, the joints can allow the foot to move translationally and/or rotationally relative to the adapter about at least two joints (e.g., pivot points). In some embodiments, the prosthetic foot is coupled to the adapter via a linkage assembly including one or more links extending generally horizontally between the joints on the foot and adapter. The joints and links can be provided in various configurations allowing the ankle module to perform different functions, for example, dorsiflexion, plantar flexion, and/or shock absorption at various stages of the user's gait cycle. In some embodiments, the ankle module further includes a support spring extending between the adapter and foot to limit the range of motion of the adapter during use, provide additional shock absorption, and improve energy storage and return.

In some embodiments, such as the example embodiment illustrated in FIG. 1A, the ankle module 300 includes two joints 310 on each of the medial and lateral sides of both the foot 100 and adapter 200, for a total of eight joints. The linkage assembly coupling the foot to the adapter includes a four bar linkage having two bars or links on each of the medial and lateral sides of the ankle. In one embodiment, the links can be pivotably coupled to the foot and adapter at the joints, allowing relative movement between the foot and adapter during ambulation. In another embodiment, the links are not pivotably coupled to the foot and/or adapter, but flex to allow for relative motion between the foot and adapter.

Figure 1B:
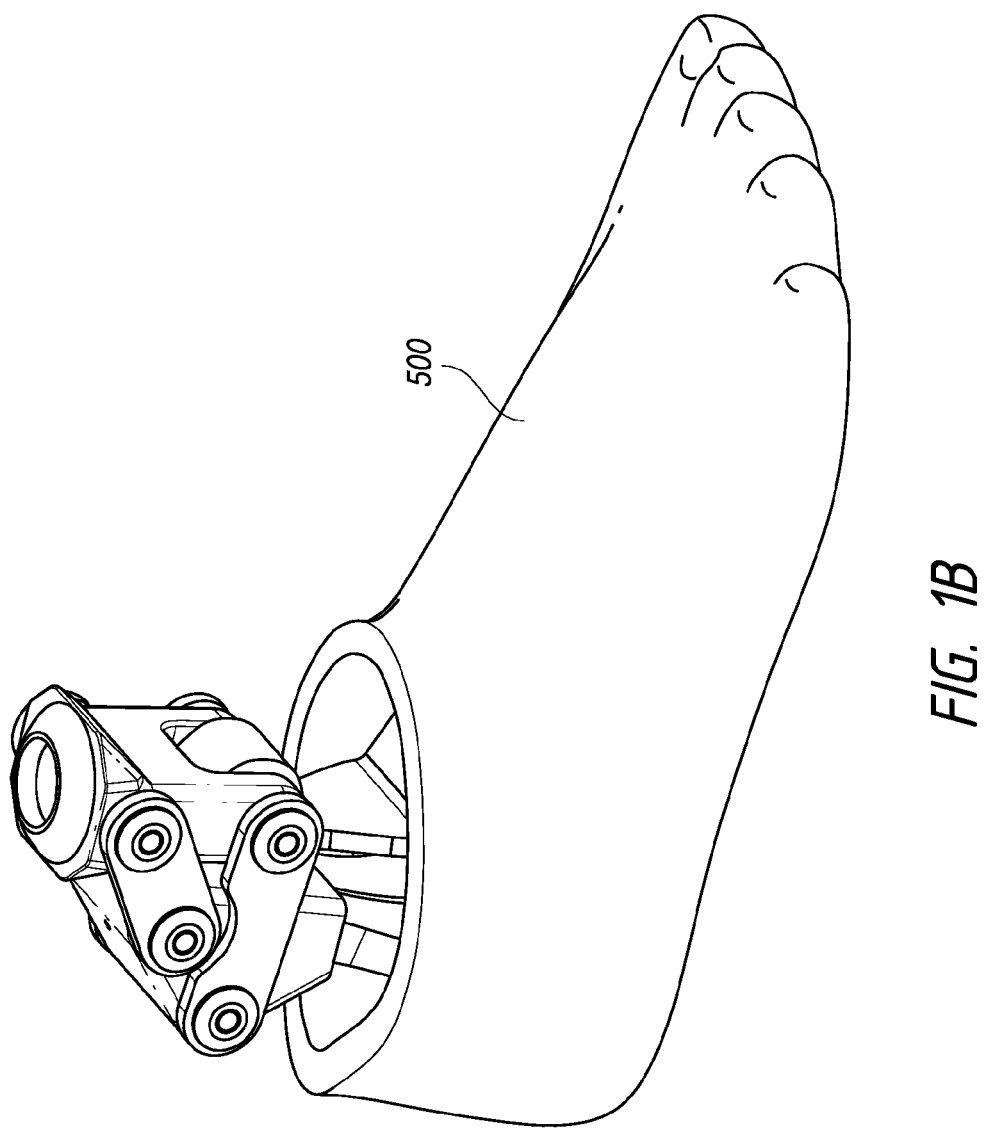
FIGS. 1B and 1C schematically illustrate the foot assembly of FIG. 1A in a cosmesis cover.
Figure 2A:
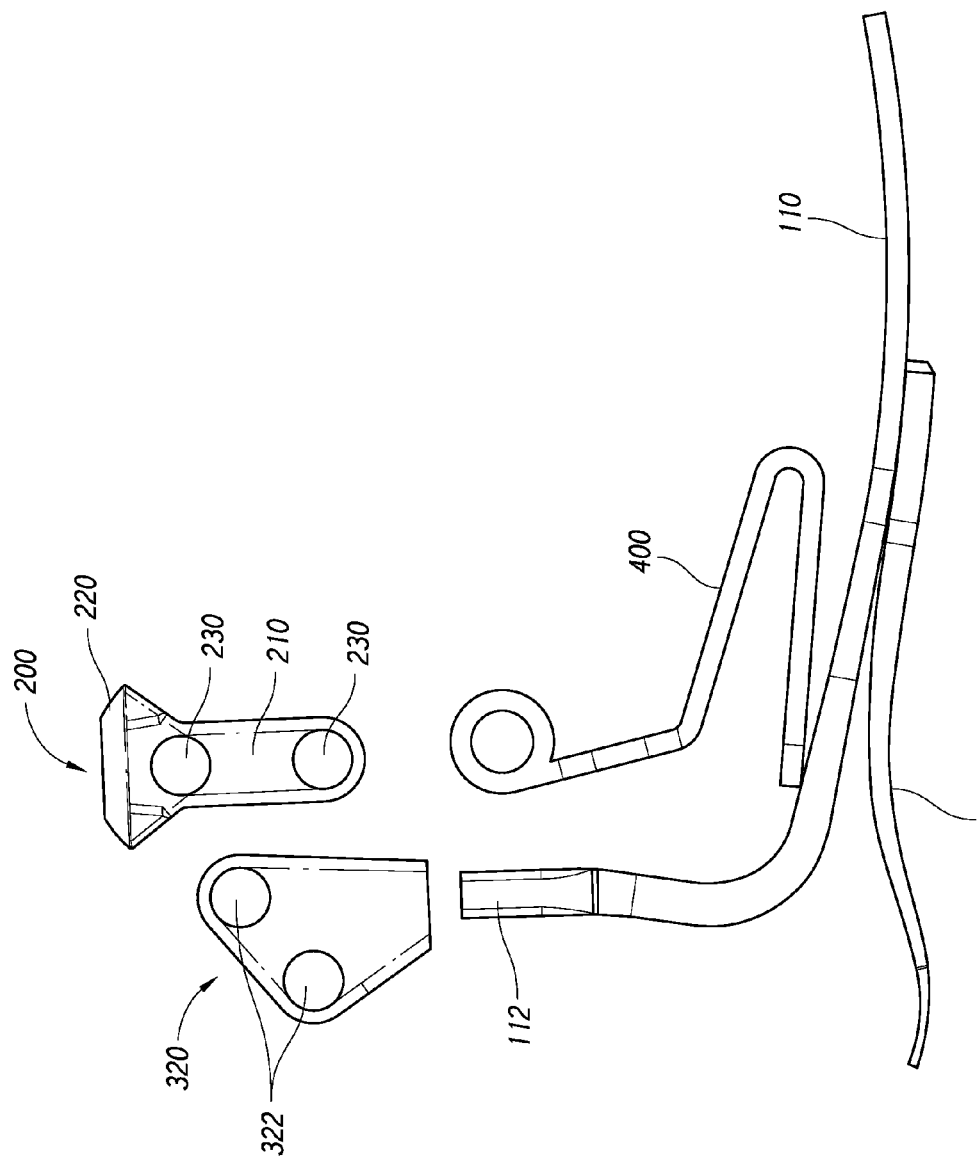
FIGS. 2A-2B schematically illustrate exploded views of the foot assembly of FIG. 1A.
Figure 2B:
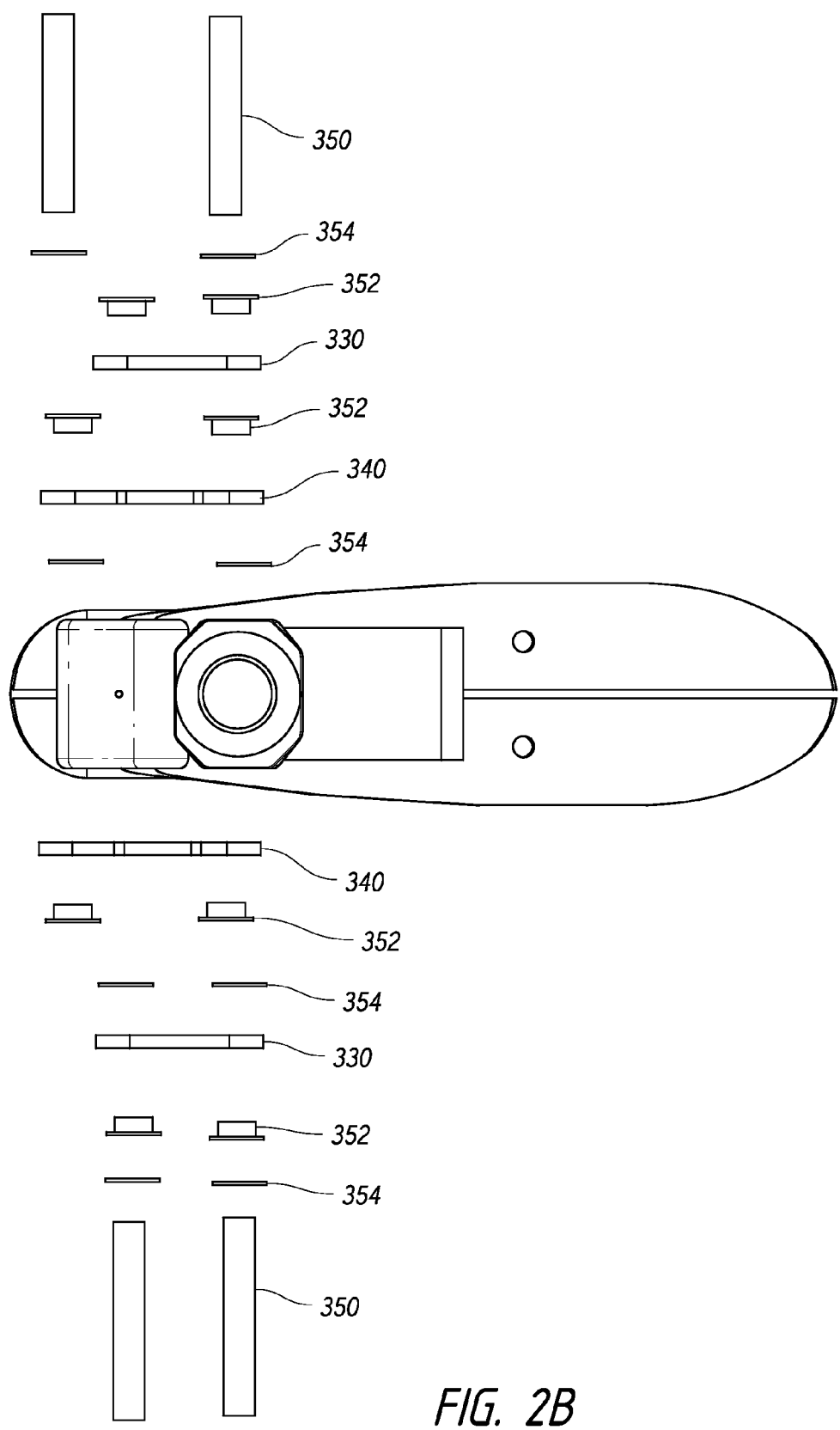

The example prosthetic foot assembly shown in FIG. 1A and the exploded views of FIGS. 2A and 2B includes a prosthetic foot 100, a connection sleeve 320, an adapter 200, two top links 330, two bottom links 340, and a support spring 400. In the illustrated embodiment, the foot 100 includes a foot member 110 extending from a generally vertically-oriented attachment section 112 downwards and forwards to a distal toe end 114 and a heel member 120 extending from a distal end 124 rearwardly to a free, cantilevered proximal heel end 122. A portion of the heel member 120 proximate the distal end 124 is coupled to the foot member 110 between the attachment section 112 and toe end 114. However, other types of prosthetic feet can also be used with the ankle module described herein.

The illustrated adapter 200 includes a generally vertical elongate body 210 and a connector, such as a male pyramid 220, configured to be coupled to a corresponding connector of a prosthetic socket or another prosthetic component, such as a pylon. However, the adapter 200 can have other configurations and include types of connectors other than a male pyramid. The adapter 200 also includes two bores 230 extending generally horizontally through the adapter 200. The top 330 and bottom 340 links, illustrated in FIG. 2C, are generally elongate bars having an aperture proximate each end. In some embodiments, the apertures have diameters of about 12.8 mm. The links 330, 340 can have the same or varying lengths and configurations. In some embodiments, the links are selected and/or designed to be able to withstand forces of up to about $1.31*10^4$ N in use. In some embodiments, the links are made of carbon fiber. However, the links can be made of other suitable materials and designed to withstand forces higher than noted above.

As illustrated in FIGS. 2D-2F, the connection sleeve 320 includes an interior cavity 324 configured to receive the attachment section 112 of the foot member 110. The connection sleeve 320 also includes two bores 322 extending generally horizontally through the connection sleeve 320. In some embodiments, the connection sleeve 320 is made of aluminum. However, other suitable materials can be used. FIG. 2E is a cross-sectional view of the connection sleeve 320 along a coronal or frontal plane, and FIG. 2F is a cross-sectional view of the connection sleeve 320 along a sagittal plane.

To assemble the ankle module 300, the connection sleeve 320 is placed on the attachment section 112 of the prosthetic foot 100 as shown in FIG. 2G. In some embodiments, screws are inserted into apertures 326 to secure the connection sleeve 320 to the foot member 110. Additionally or alternatively, glue or another adhesive can be introduced into the cavity 324 via aperture 328 to secure the connection sleeve 320 to the foot member 110. An aperture 327 in a top surface of the connection sleeve 320 can allow for air to escape the cavity 324 as glue or another adhesive is introduced into the cavity 324.

Figure 2I:
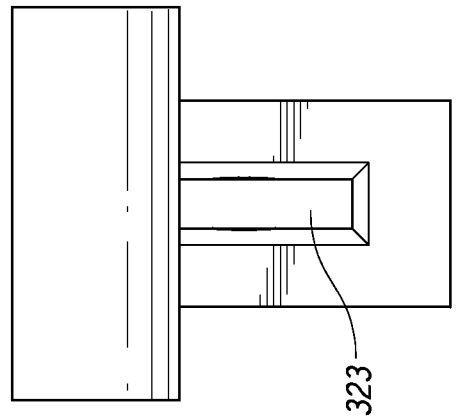
FIGS. 2H-2I schematically illustrate another embodiment of a connection sleeve.
Figure 2H:
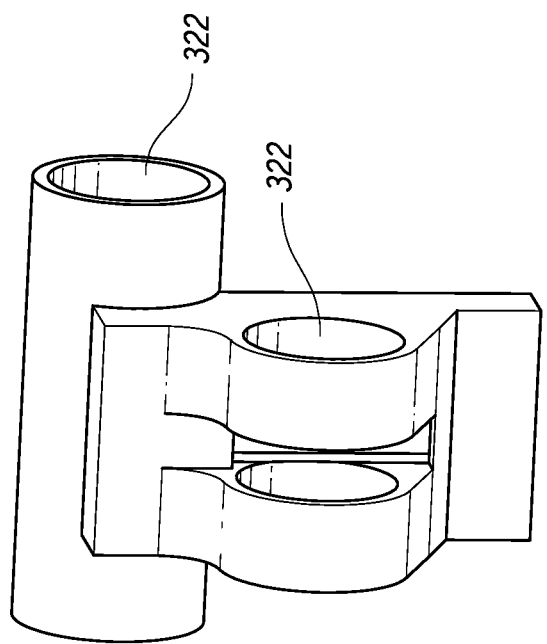
Figures 2J, 2K:
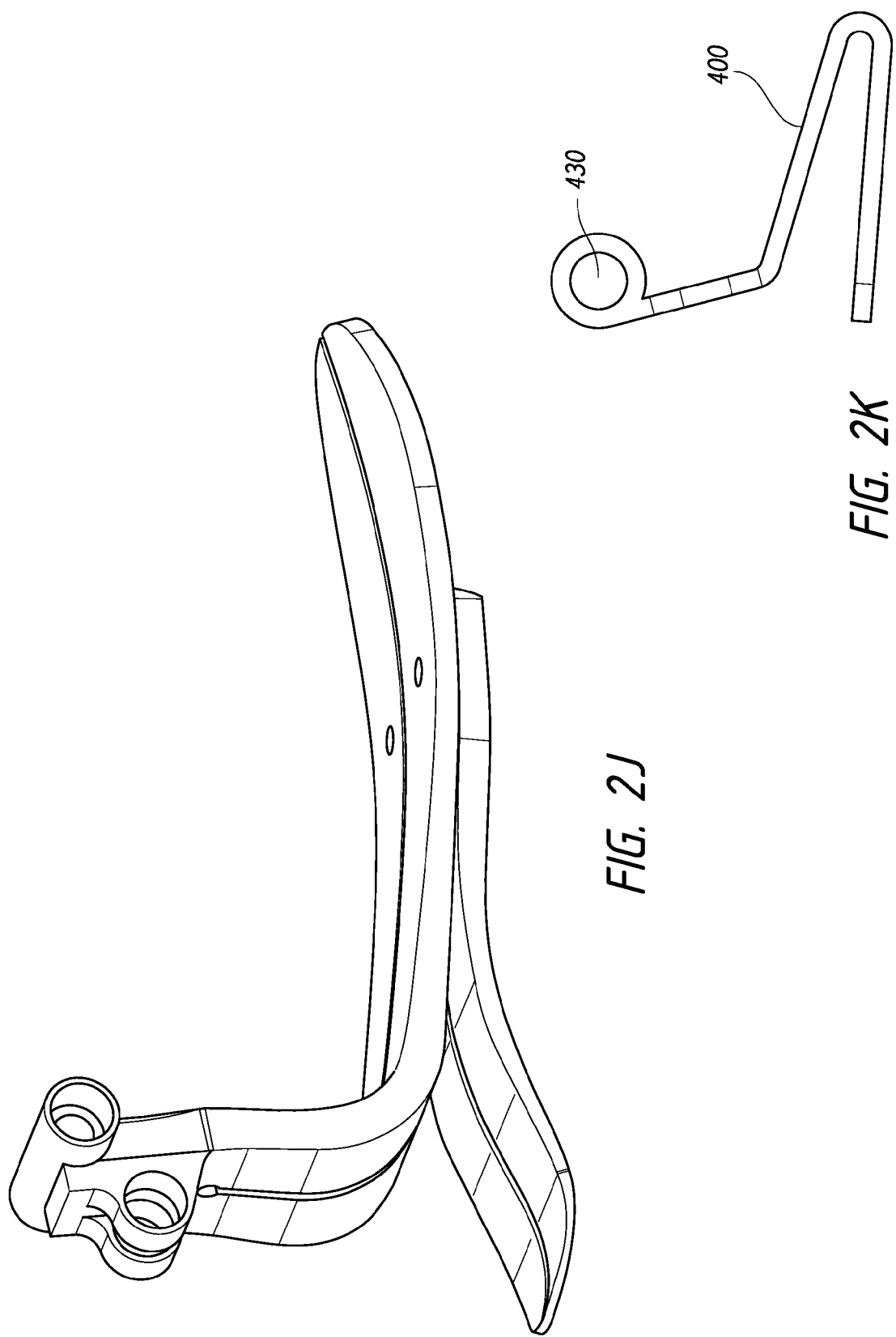
FIG. 2J schematically illustrates the connection sleeve of FIGS. 2H-2I coupled to a prosthetic foot.
FIG. 2K schematically illustrates a support spring of the foot assembly of FIG. 1A.

FIGS. 2H-2J illustrate an alternative embodiment of a connection sleeve 320. In this embodiment, the connection sleeve 320 is integrated with the attachment portion 112 of the foot member 110. This connection sleeve 320 can be integrally (e.g., monolithically) formed with the attachment portion 112 or glued onto the attachment portion 112. The connection sleeve 320 can further include a vertical slot 323. This alternative connection sleeve 320 can advantageously be smaller and/or lighter.

The links 330, 340 are arranged so that each link extends between the connection sleeve 320 and the adapter 200 and the apertures in the links 330, 340 are aligned with the bores 322, 230 through the connection sleeve 320 and adapter 200, respectively. In some embodiments having the alternative connection sleeve of FIGS. 2H-2J, the linkage assembly can include a single bottom link 340 that extends through the slot 323 to align with the connection sleeve 320 bore 322. The links 330, 340 are coupled to the connection sleeve 320 and adapter 200 via pins 350. Each pin 350 extends through an aperture in a link 330, 340, a bore 230, 322 in the adapter 200 or connection sleeve 320, respectively, and an aperture in another link 330, 340. Bushings 352 and washers 354 can also be placed along the pins 350 to help protect the link apertures and pins 350 from wear and create the joints 310 that allow for pivotal movement of the links 330, 340, as shown in the illustrated embodiment. In some embodiments, pin roller bearings are used instead of bushings to provide improved wear resistance.

Figure 2M:
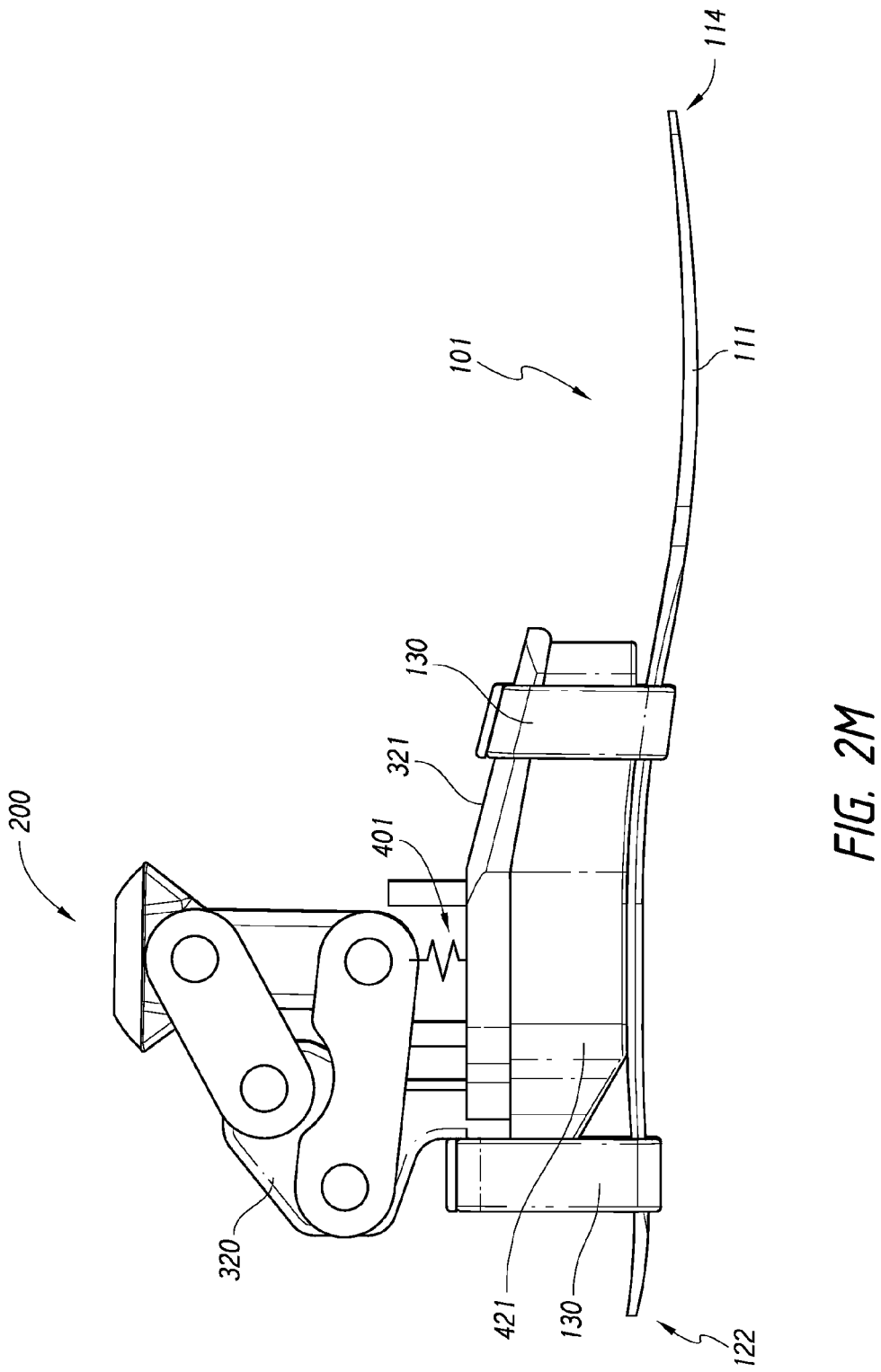
FIG. 2M schematically illustrates an example embodiment of a foot assembly having an ankle module.

In some embodiments, an ankle module 300 can be used with other types of prosthetic feet, for example, prosthetic foot 101 shown in the example embodiment illustrated in FIG. 2M. As shown, prosthetic foot 101 includes a foot member 111 extending from a proximal heel end 122 to a distal toe end 114. In the illustrated embodiment, the connection sleeve 320 includes a base 321, so that the connection sleeve 320 and base 321 are one piece. In another embodiment, the connection sleeve 320 and base 321 can be separate components coupled to each other. When the prosthetic foot 101 is assembled, the base 321 of the connection sleeve 320 is placed on a block 421, which is placed on a top surface of the foot member 111. The block 421 can be of a resilient material (e.g., foam). The block 421 can advantageously allow for multi-axial movement of the foot during use. In some embodiments, the base 321 and block 421 and/or the block 421 and foot member 111 are coupled with an adhesive, e.g., glue. Additionally or alternatively, the base 321, block 421, and foot member 111 can be secured with one or more straps 130 extending around a top of the base 321 and bottom of the foot member 111 as shown in FIG. 2M. In some such embodiments, the straps 130 can be made of an elastic material to allow for flexion of the prosthetic foot 101 during use. The example prosthetic foot 101 of FIG. 2M can advantageously be appropriate for low-activity users. Such users may require or prefer stability and/or comfort over high performance and/or energy return, but may still benefit from various features the ankle module 300 can provide, for example, dorsiflexion, plantar flexion, and/or shock absorption at various stages of the user's gait cycle. In some embodiments, the prosthetic foot 101 also includes a spring 401 extending between the base 321 of the coupling sleeve 320 and the adapter 200. Instead of or in addition to the spring 401, the foot 101 can include a damper (e.g., hydraulic damper) between the base 321 and the adapter 200. The spring 401 and/or damper can help limit and/or control movement or the adapter 200 to provide a less dynamic and/or more stable foot for low activity users. Advantageously, the foot 101 dorsiflexes at toe-off for toe clearance during the swing phase of gait.

In use, the adapter is fixed relative to the user, and the foot translates and/or rotates (e.g., moves along an arcuate path disposed on a circle aligned with a longitudinal axis of the foot) relative to the adapter during ambulation. The movement of the foot about the adapter is based on the location of a ground reaction force applied to the foot during ambulation relative to an instantaneous center of rotation for the foot. The location of the foot's instantaneous center of rotation depends on the particular characteristics and arrangement of the links in the linkage assembly. In some embodiments, the center of rotation is located at a point where lines projected in either direction from the ends of the top and bottom links cross. In use, the instantaneous center of rotation can change as the user progresses through the stages of the gait cycle because as the foot moves relative to the adapter, the links pivot at the joints on the foot and adapter and the orientation of the top and bottom links relative to each other can change. As the crossing point and therefore the center of rotation move farther away from the foot, the arc of rotation of the foot about the adapter flattens, resulting in more translational movement and less rotational movement. If the center of rotation is infinitely far away from the foot, for example, if the top and bottom links are parallel and of equal length, the foot may only translate and not rotate relative to the adapter.

FIG. 3 illustrates two hypothetical linkage assembly arrangements and the results of application of three different ground reaction forces to the feet. The dots represent the instantaneous center of rotation, the straight arrows and dashed lines show the ground reaction forces during different stages of the stance phase of the gait cycle, and the curved arrows near the dots illustrate the direction of rotation of the foot about the center of rotation. The linkage assembly arrangement of A-C causes the center of rotation to be in front of the foot, whereas the center of rotation is behind the foot with the linkage assembly arrangement of D-F. A and D show the ground reaction forces at heel strike, B and E show the forces and mid-stance, and C and F show the forces at toe off. The ground reaction forces in A, B, and D are behind the center of rotation, causing a clockwise rotation and plantarflexion of the foot. The ground reaction forces in C, E, and F are in front of the center of rotation, causing a counterclockwise rotation and dorsal flexion of the foot.

Varying the number, length, and/or orientation of the links 330, 340 can therefore cause the ankle module 300 and foot 100 to act differently and provide different benefits in various stages of the gait cycle. In the example embodiment illustrated in FIG. 1A, the upper 330 and lower 340 links have different lengths and are orientated non-parallel to each other. This configuration can promote dorsiflexion through mid-stance and plantar flexion at toe off. In various embodiments, the links 330, 340 can be selected and arranged to achieve certain desired functions and advantages such as: plantar and/or dorsal flexion, for example, dorsiflexion during stance and/or plantarflexion at toe off, vertical shock absorption, rotation of the foot in the transverse (horizontal) plane or about the sagittal axis, inversion and/or eversion, toe clearance during the swing phase of the gait cycle, for example, via dorsiflexion during swing, and/or heel height adjustment. For example, the foot 101 illustrated in FIG. 2M can provide dorsiflexion upon toe-off to allow for toe clearance during swing for low active users.

Linkage Assemblies

FIGS. 4A-4I illustrate schematics and example embodiments of various possible linkage assembly arrangements. Of course these are only example arrangements, and others are also possible. Furthermore, although certain functions are described for each arrangement, other functions may result from a particular arrangement in addition to or instead of the functions described, for example, depending on the actual lengths, arrangements, angles, and other characteristics of the links selected for a given implementation of these concepts.

In the arrangement of FIG. 4A, the top links T and bottom links B are parallel and have equal lengths. The instantaneous center of rotation is therefore at infinity, so the foot translates but does not significantly rotate about the adapter. This arrangement advantageously provides vertical shock absorption when the foot is loaded and vertical motion back to neutral upon unloading. The top T and bottom B links are parallel in the arrangements of FIGS. 4B and 4C as well. However, in the arrangement of FIG. 4B, the top links T are longer than the bottom links B, and in the arrangement of FIG. 4C, the top links T are shorter than the bottom links B. Due to the parallel orientation of the links, the center of rotation is at infinity so the foot translates but does not rotate upon initial loading, providing vertical shock absorption in both arrangements. In some embodiments having shorter bottom links B as in the arrangement of FIG. 4B, the foot has a center of rotation behind the foot during stance, causing dorsiflexion. Dorsiflexion during stance can advantageously provide the user with more freedom on the foot, as the dorsiflexion helps stiffen the foot providing stability and helping prevent the user from falling. During unloading, the foot may plantarflex then provide vertical motion back to neutral. The foot assembly embodiment 100B shown on the right of FIG. 4B also includes a bumper 360 located within the linkage assembly. The bumper 360 can be made of a resilient material (e.g., rubber) and can advantageously help stiffen the foot during at least a portion of gait (e.g., during dorsiflexion). In some embodiments having shorter top links T as in the arrangement of FIG. 4C, the center of rotation is in front of the foot during stance, causing plantarflexion. During unloading, the foot may dorsiflex then provide vertical motion back to neutral. Dorsiflexion upon unloading prior to the swing phase can also advantageously provide toe clearance during swing. However, because the top T and bottom B links are parallel, the center of rotation may be distant from the foot, resulting in greater translational and less rotational movement.

Figure 4E:
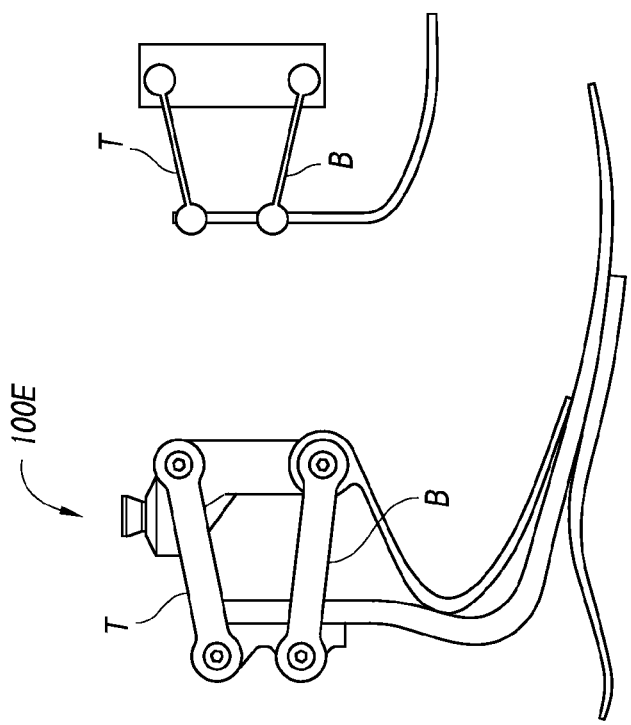
Figure 4D:
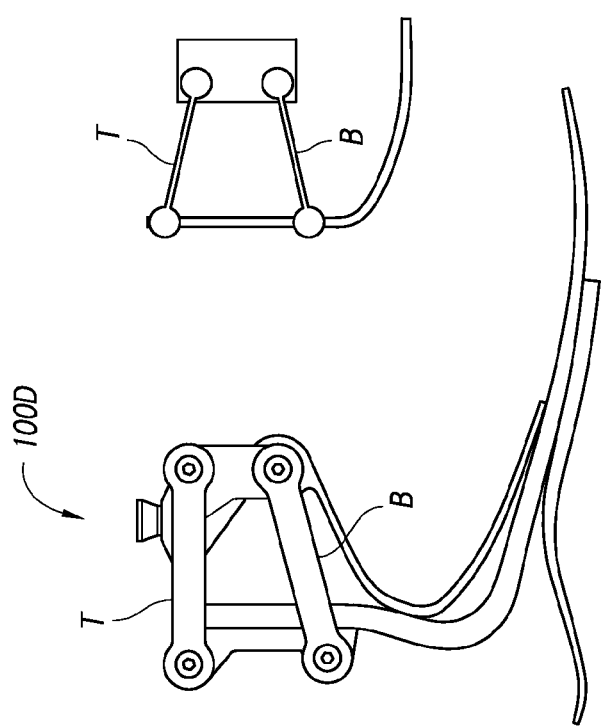

In the example arrangements of FIGS. 4D-4I, the top links T and bottom links B are non-parallel to each other. This often allows for greater rotational motion compared to arrangements having parallel top and bottom links. In the arrangement of FIG. 4D, the top T and bottom B links have substantially equal lengths. The front or distal ends of the top T and bottom B links are angled toward one another, so the center of rotation is in front of the foot. The foot therefore plantarflexes upon loading and during stance, then dorsiflexes during toe off and upon unloading. As mentioned above, dorsiflexion during pre-swing can advantageously provide for toe clearance during swing. Furthermore, with a linkage arrangement that produces plantarflexion when loaded, the foot can be aligned so that it is slightly dorsiflexed when unloaded to allow for improved toe clearance during swing, for example as shown in FIGS. 4J-4K. With such an alignment, the foot can plantarflex to a desired alignment upon heel contact and then advantageously dorsiflex back to its unloaded alignment at toe off to provide the toe clearance during the swing phase of the gait cycle. In the arrangement of FIG. 4E, the top T and bottom B links also have substantially equal lengths, but the rear or proximal ends of the links are angled toward one another, so the center of rotation is behind the foot. In some embodiments, a foot having such an arrangement may dorsiflex upon loading and during stance and plantarflex during unloading.

Figure 4F:
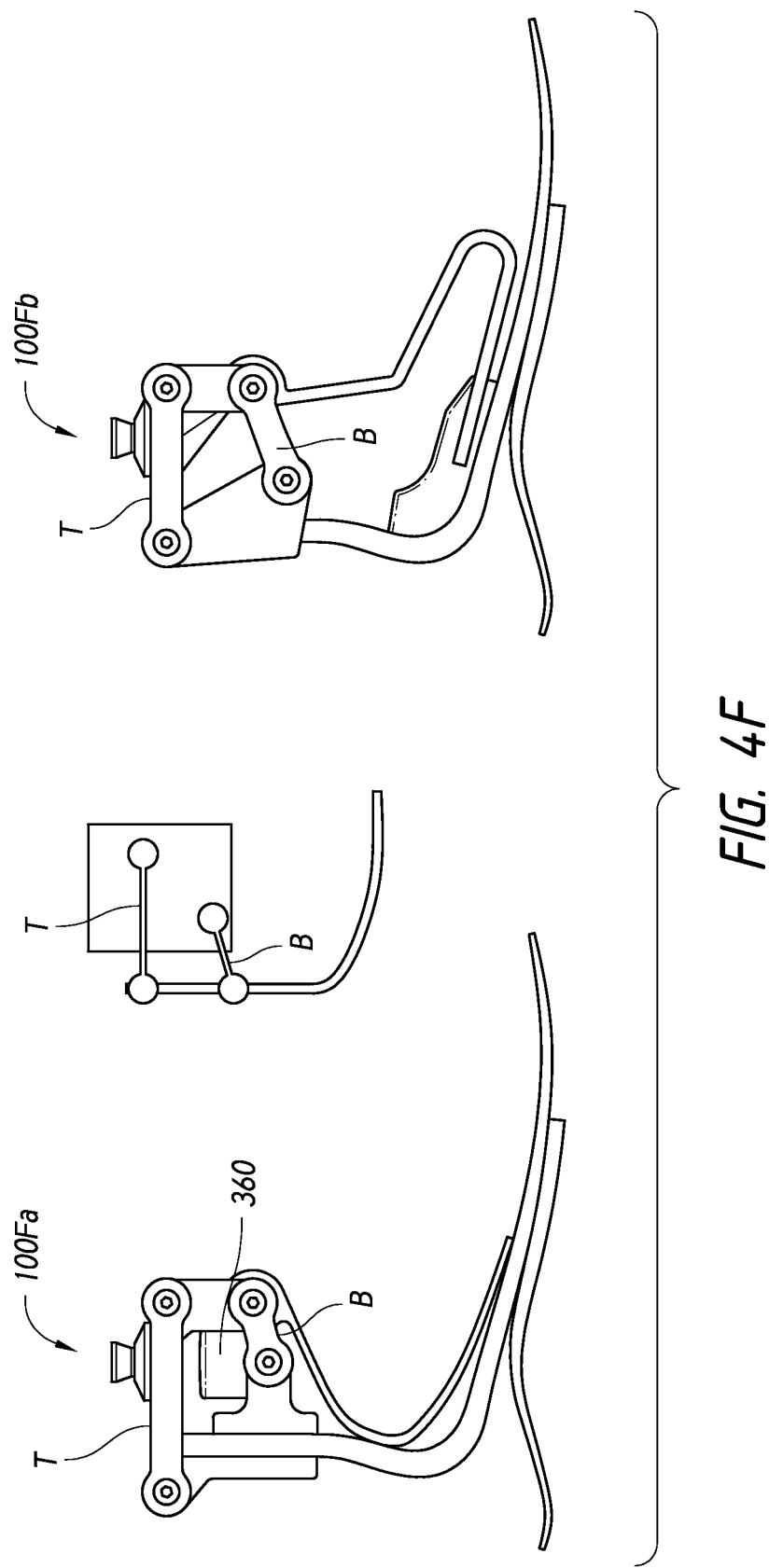
Figure 4H:
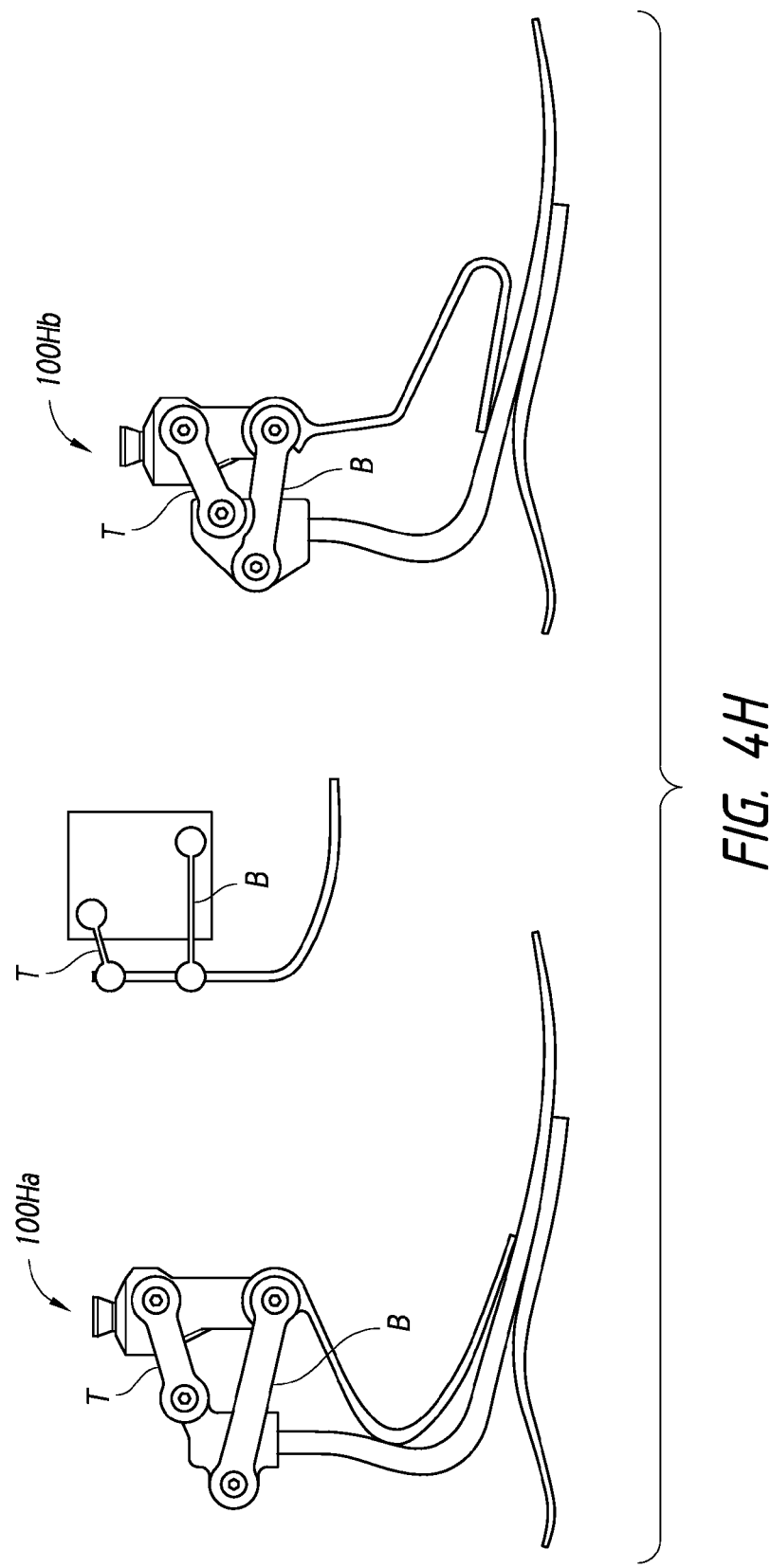
Figure 41:
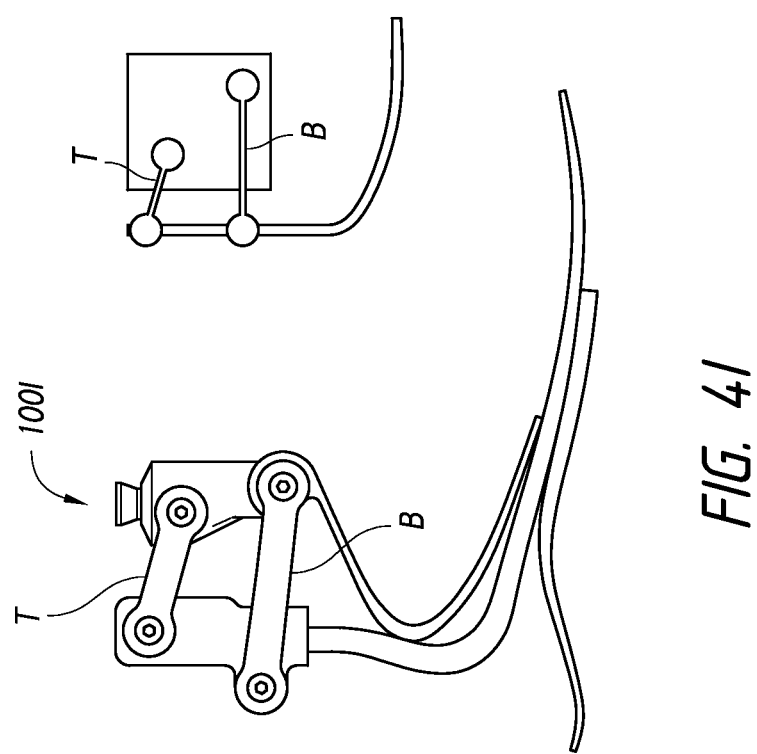
Figure 4K:
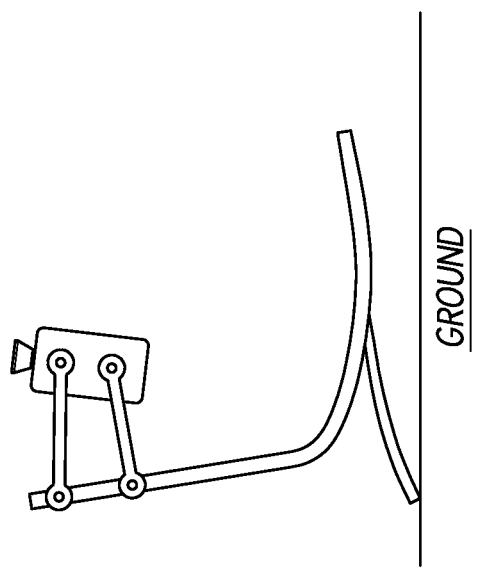
FIGS. 4J-4K schematically illustrate a prosthetic foot assembly having a linkage that allows for plantarflexion when loaded.
Figure 4J:
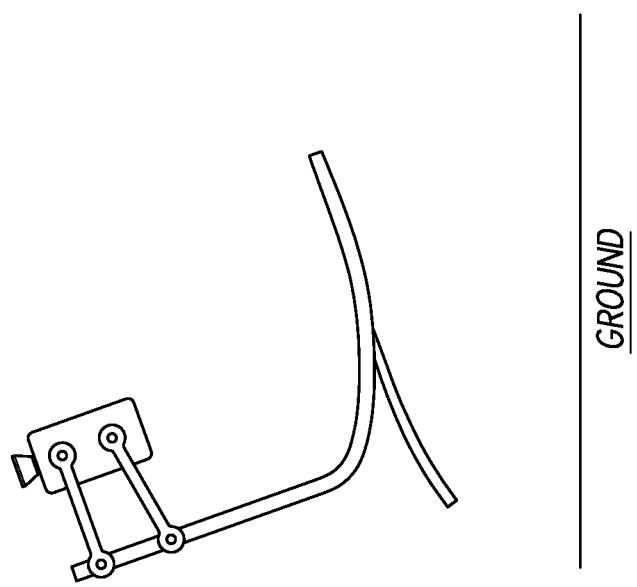
Figure 4L:
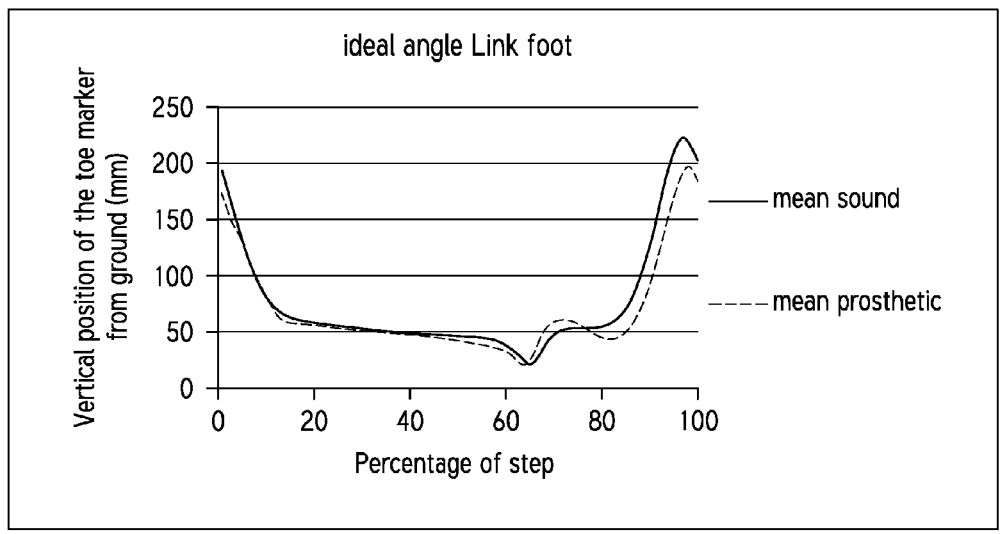
FIG. 4L illustrates a graph showing toe position of the foot of FIG. 4H and of the sound leg during the gait cycle.
Figure 4M:
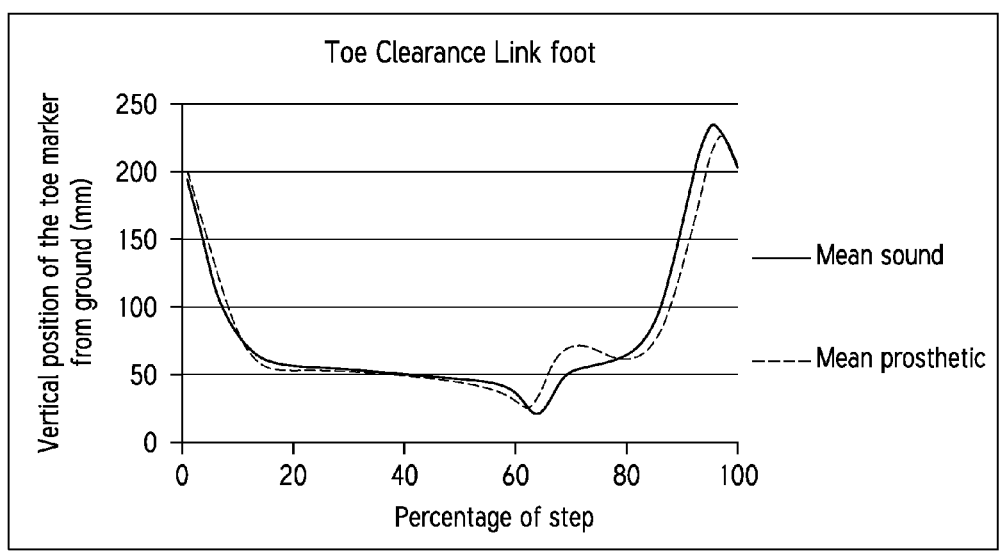
FIG. 4M illustrates a graph showing toe position of the foot of FIG. 4F and of the sound leg during the gait cycle.

In example arrangements of FIGS. 4F-4I, the top links T and bottom links B have un-equal lengths. In the arrangements of FIG. 4F, the bottom link B is shorter than the top link T, and the center of rotation is on the foot. During loading the center of rotation is in front of the ground reaction force, producing plantar flexion. In some embodiments, this arrangement provides vertical shock absorption during mid-stance and vertical motion back to neutral and dorsiflexion on unloading, which can provide toe clearance in swing. For example, at a point about 80% into the user's gait cycle (during swing), the toe might clear the ground by a vertical distance of about 15 mm more than an alternative foot, for example, a foot such as the example embodiment shown in FIG. 4H. FIG. 4L illustrates a graph showing the vertical position of a marker on the toe of the foot of FIG. 4H over the course of the gait cycle compared to the vertical position of a marker on the toe of the sound leg. FIG. 4M illustrates a graph of the vertical position of the toe of the foot of FIG. 4F compared to the sound leg. In these graphs, toe-off occurs at a point about 65% into the step. This is the lowest point of the graph because the marker rotates over the toe toward the ground during toe-off. The following peak occurs when the foot is behind the user's body, and the foot passes through the center to move in front of the body at about 80%. The point at which the foot passes through center (about 80%) is important as it is the point during swing at which the foot and toe come closest to the ground and ensuring toe clearance is most needed. The vertical shock can result from movement of the foot and ankle assembly that causes the top and bottom links to become closer to parallel. In some embodiments however, the foot dorsiflexes during stance then again plantar flexes upon unloading. Dorsiflexion during stance can help a user move over the foot more easily during ambulation and provide a smoother or improved rollover. This can be the result of less motion of the links so that they remain non-parallel, which can be accomplished by a stiffer foot and/or support spring. Plantar flexion during toe off and unloading can advantageously provide an improved push off and a softer toe feel for users. Plantar flexion can be achieved if the ground reaction force crosses the instantaneous point of rotation during ambulation. The foot assembly embodiment 100Fa shown in the center of FIG. 4F also includes a bumper 360 located within the linkage assembly. The bumper 360 advantageously helps inhibit excess dorsal flexion of the foot, similar to the stiffening of an able-bodied gait during ambulation. In the arrangement of FIG. 4G, the center of rotation can be behind the foot, resulting in dorsiflexion during loading a midstance and plantarflexion during unloading. In the arrangement of FIG. 4H, the center of rotation can again be behind the foot, providing dorsiflexion during loading and plantar flexion during unloading. Depending on the distance of the center of rotation from the foot, during certain phase of the gait cycle, such as mid-stance and terminal stance, the center of rotation may approach infinity, providing vertical shock absorption and vertical motion back to neutral during those phases. In the example embodiment 100Hb shown on the right of FIG. 4H, the center of rotation starts close behind the foot, allowing for slight plantar flexion at heel strike, and shifts farther away from the foot during stance. As the center of rotation moves farther away, the foot rotates less and translates more, allowing for dorsiflexion during loading followed by progressive stiffening of the foot through stance. In some embodiments, this linkage arrangement allows for dorsal flexion of up to about 10-15° and about 10 mm of vertical motion. In some embodiments, the arrangement of FIG. 4H provides push off at toe off and may provide greater push off than, for example, the arrangement of FIG. 4F. In the arrangement of FIG. 4I, the center of rotation is in front of the foot, providing plantar flexion during loading and midstance, and dorsiflexion during unloading.

Three-Dimensional Motion

In some embodiments, the ankle module 300 can be configured to allow for three-dimensional motion in and about different anatomical planes and axes during ambulation. For example, in some embodiments, the ankle module 300 includes three links, e.g., two top links 330 and one bottom link 340 as shown in FIGS. 5A and 5B or one top link and two bottom links. In the illustrated embodiment, the top 330 and bottom 340 links are parallel. However, the configurations illustrated in FIGS. 4A-4I and described herein or other arrangements are also possible. In some embodiments, a link or links on the medial side of the ankle can be aligned along a different axis than a link or links on the lateral side of the ankle (i.e., links on the medial and lateral sides can be non-parallel in the sagittal plane). Links on the medial and lateral sides of the ankle can have the same or different lengths. In some embodiments, the links are flexible. These features can allow the adapter 200 to rotate clockwise or counterclockwise in the transverse plane during ambulation. For example, a longer link on the medial side of the foot can cause clockwise rotation of the adapter 200 (e.g., rotation in a clockwise direction when viewed from the front of the prosthetic foot). In some embodiments, this rotation can help guide the foot in a medial to lateral or lateral to medial direction during ambulation to help produce a smoother and more natural rollover.

Figure 6B:
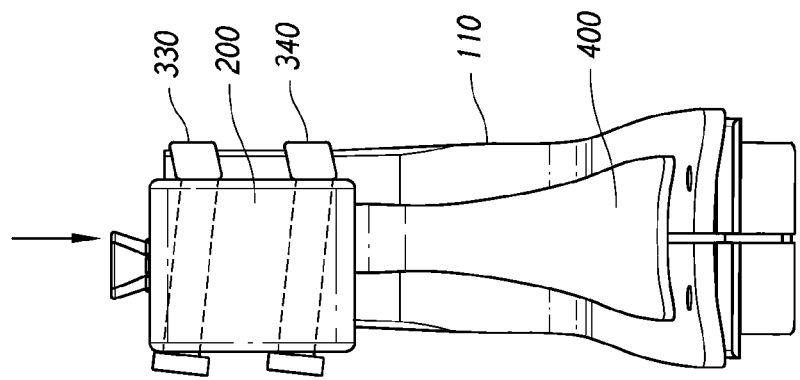
Figure 6A:
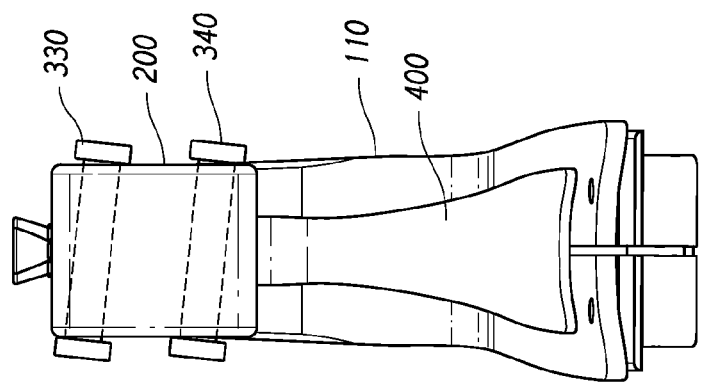
Figure 8:
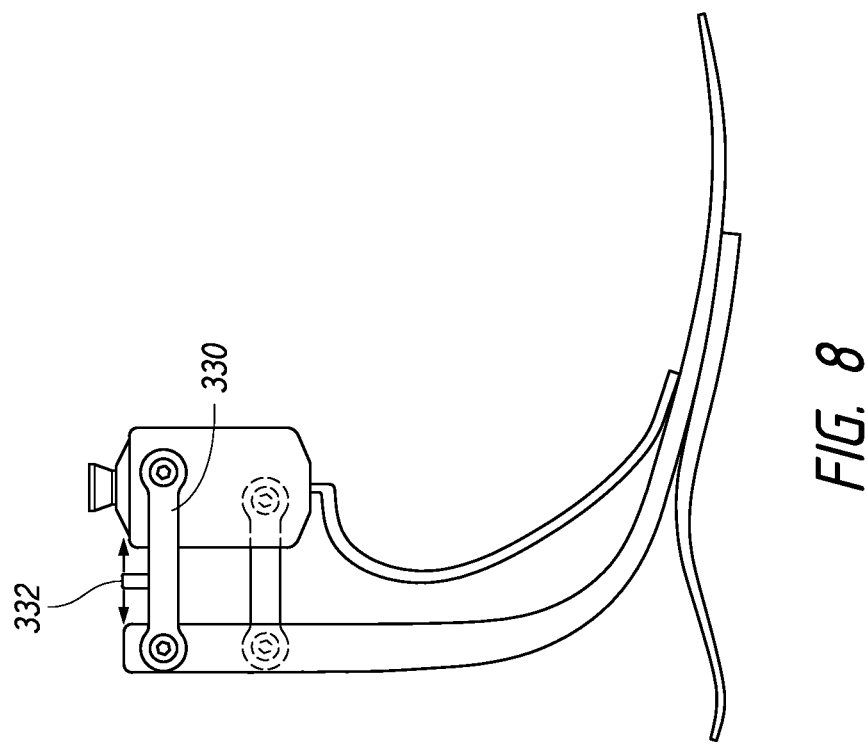
Figure 7A:
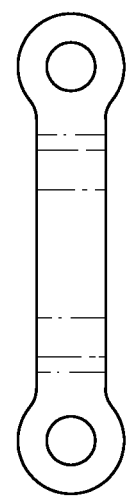
FIGS. 7A and 7B schematically illustrate an alternative link embodiment.
Figure 7B:

In some embodiments, the ankle module 300 includes four links and the two links on one side (medial or lateral) of the ankle are shorter than the two links on the other side. This can produce inversion or eversion of the adapter 200 (rotation of the adapter 200 about the coronal axis) during ambulation. In some embodiments, for example as shown in FIGS. 6A and 6B, links on the medial and lateral sides are offset from or aligned at an angle to one another when viewed from the front or back. This causes movement of the adapter 200 in the medial or lateral direction (movement in the coronal plane or movement into or out of the sagittal plane) during ambulation. In some embodiments, the links have spring-like properties, allowing movement of the adapter 200 in the sagittal plane (towards or away from the foot 100) and/or twisting of the adapter 200. For example, the links can be made of carbon fiber and can include an arch as shown in FIGS. 7A and 7B to allow the ends of the links to move toward and away from each other. In some embodiments, one or more links can have an adjustable length. For example, the embodiment of a linkage assembly shown in FIG. 8 includes a shifter 332 that allows for adjustment of the length of the link 330. The links can be adjusted via manual, electrical, pneumatic, or any other suitable means.

Additional Features and Alternative Linkages

In some embodiments, the ankle module 300 can incorporate additional features. For example, the ankle module 300 can include a stance break or swing break mechanism. Such a mechanism can selectively lock the foot 100, adapter 200, and/or ankle module relative to each other to inhibit the properties and functions of the particular linkage assembly or ankle module and allow the foot 100 to function normally as it would if coupled to an adapter in a conventional manner. This can advantageously allow the ankle module and/or linkage assembly to function only during certain phases of the gait cycle. In some embodiments, the ankle module 300 can include sensors to detect the orientation of the links. The orientation of the links varies over the course of the gait cycle, so the sensor data can be processed to determine the phase of the gait cycle at a given time. This information can then be used to trigger certain actions during certain parts of the gait cycle. For example, a stance break or swing break mechanism can be activated during a certain phase of the gait cycle as determined from the sensor data.

Figure 9:
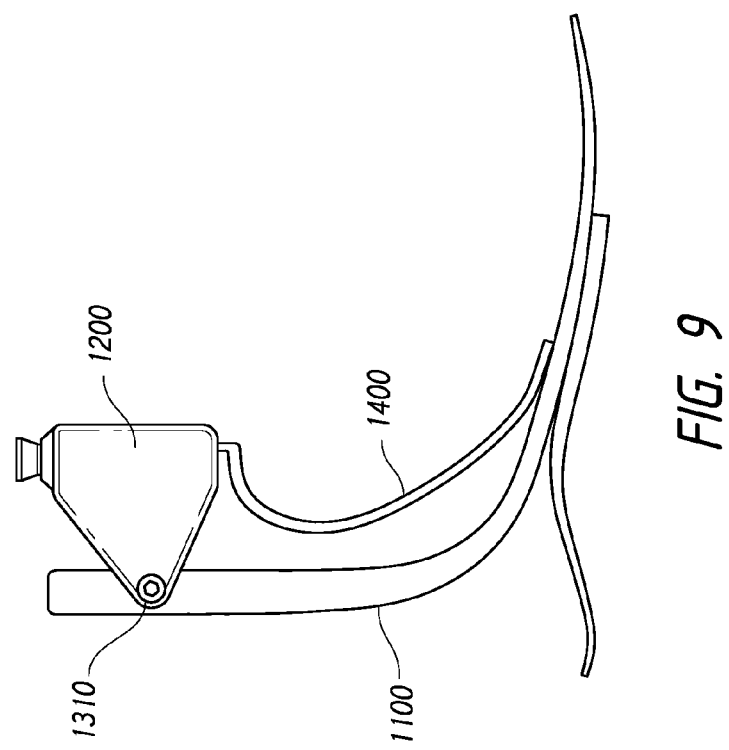

Various linkage assemblies having pivotal joints connected by a four-bar linkage have been shown and described herein. However, other linkage arrangements are also possible. For example, the foot 100 and adapter 200 can be coupled via a polymer block or wedge. The stiffness and other properties of the polymer can be selected to achieve functions similar to those provided by the various linkage assemblies. Another alternative is illustrated in FIG. 9. In this embodiment, a triangular link 1200 is coupled to the foot member 1110 at a hinge 1310 and functions as an adapter and linkage assembly simultaneously. The triangular link 1200 can be a single component or a three-bar linkage assembly. Integrated adapter linkage assemblies can have other shapes, arrangements, and orientations as well.

Figure 10A:
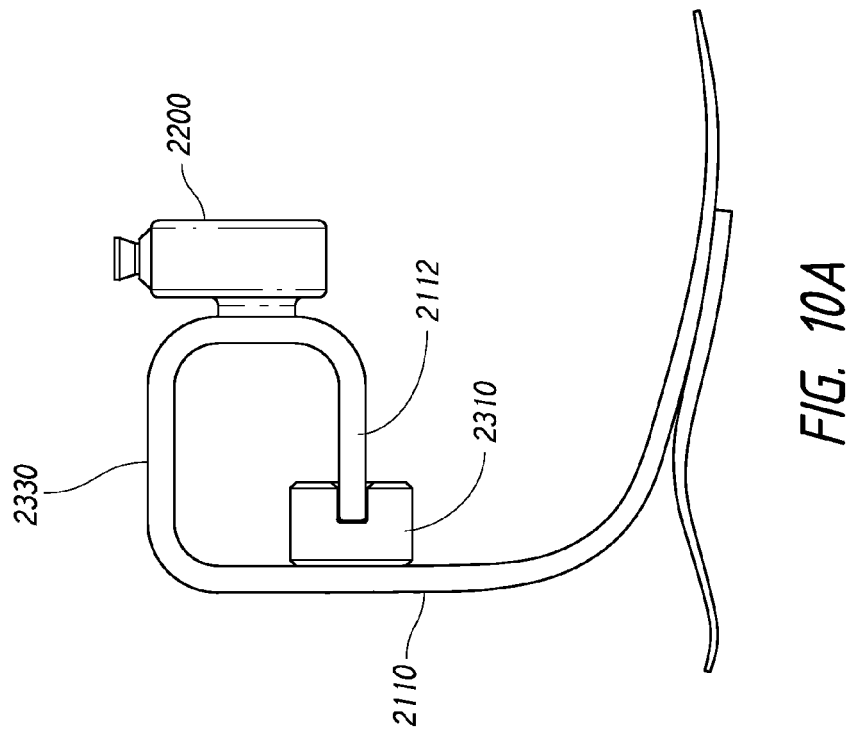

In some embodiments, for example as shown in FIG. 10A, the foot member 2110 itself is shaped to function as a link to the adapter 2200. A proximal attachment portion 2112 of the foot member 2110 can be coupled to another portion of the foot member 2110 via a connector 2310. The foot member 2110 can be made of carbon fiber or another material capable of storing and releasing energy and allowing for movement between the portion of the foot coupled to the adapter 2200 and the portion of the foot coupled to the connector 2310.

Figure 10C:
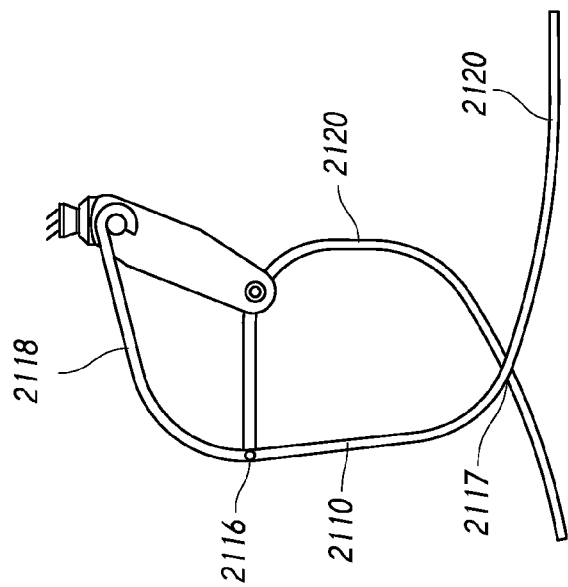
Figure 10B:
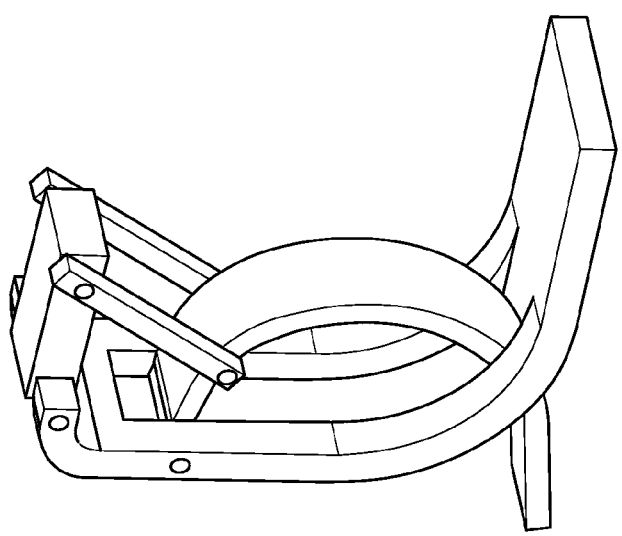

In some embodiments, for example, as shown in the schematics of FIGS. 10B and 10C, portions of both the foot member 2110 and heel member 2120 form the linkage assembly. In the illustrated embodiment, the heel member 2120 extends through an opening in the foot member 2110. The foot 2110 and heel 2120 members can be coupled via a hinge or fixed joint 2117 where the heel member 2120 extends through the foot member 2110. The hinge or joint 2117 can help adjust the degree to which loading and unloading of the foot member 2110 influences the loading/unloading and function of the heel 2120. The foot member 2110 can include a hinge 2118 to allow a portion of the foot member 2110 to function as a link, and the portion of the heel member 2120 functioning as a link can be coupled to the foot member 2110 via a hinge or joint 2116. Embodiments in which one or more bar-type links are replaced by portions of the foot member and/or heel member acting as links to the adapter can advantageously be lighter weight due to the removal of one or more bar-type links. Such embodiments also have fewer small parts and few components in general, which in some embodiments can help make the foot more robust as there are fewer components that may potentially fail.

FIG. 11 illustrates another alternative embodiment of a linkage arrangement incorporating carbon fiber or similar links 3330, 3340. In this embodiment, the links 3330, 3340 extend between the adapter 3200 and an attachment location 3320 at or near a proximal end of the foot member 3110.

Figure 13:
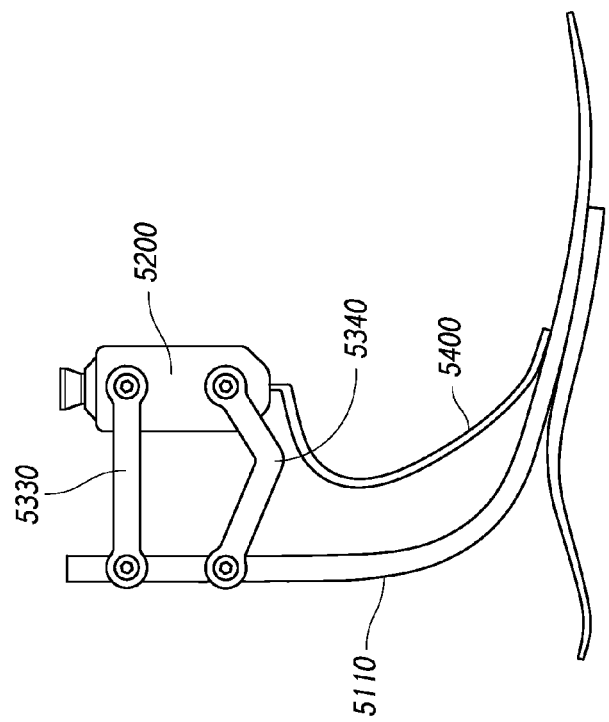
Figure 12:
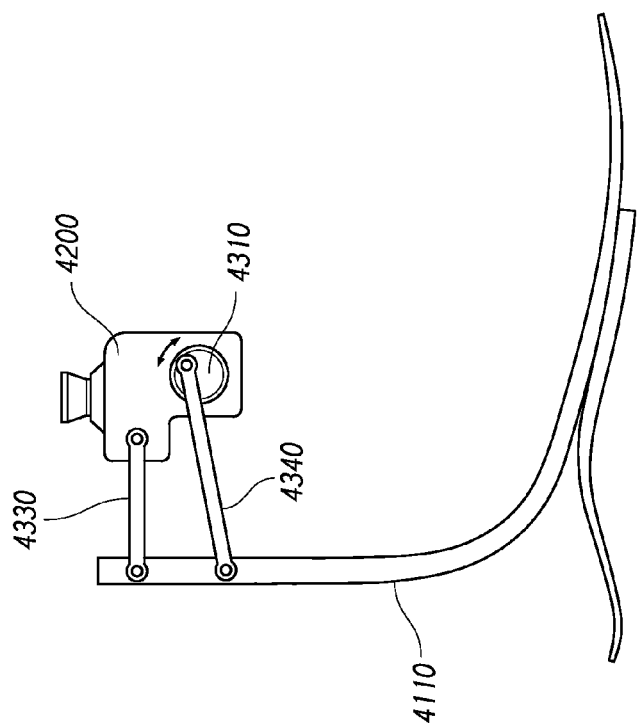

FIG. 12 illustrates an embodiment in which the adapter 4200 includes a rotating hinge joint 4310. This feature can allow for additional rotation and/or translation of the foot relative to the adapter and/or allow for ease of heel height adjustment. In some embodiments, one or more of the links can be bent, angular, arcuate, or otherwise non-linear, for example, bottom link 5340 shown in FIG. 13. Such non-linear links influence the progression of the instantaneous center of rotation of the foot during ambulation, which in turn influences the motion of the foot about the pyramid during ambulation.

Support Springs

Figure 14B:
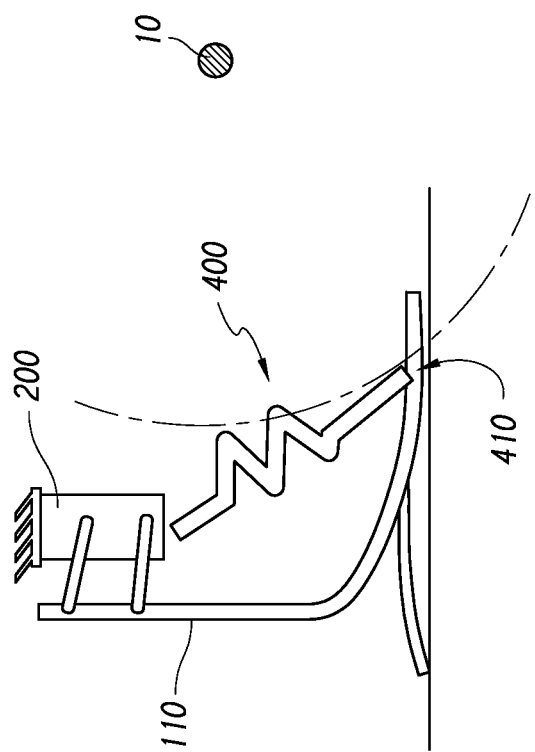
FIGS. 14A and 14B schematically illustrate the effect of different centers of rotation on compression of a support spring.
Figure 14A:
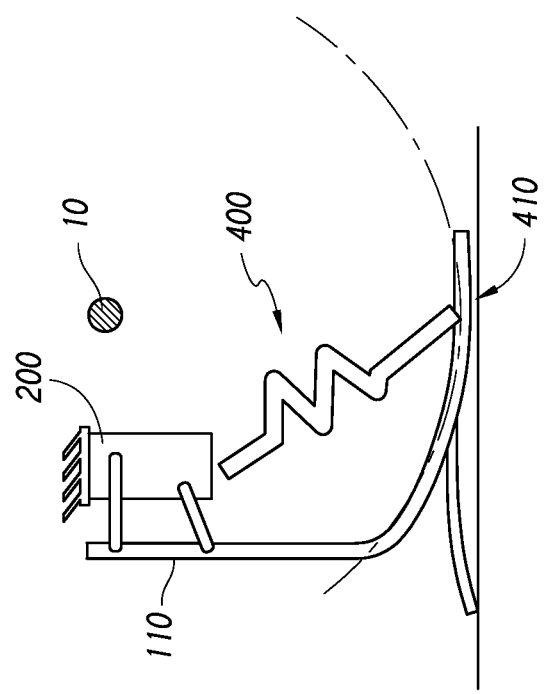

In some embodiments, the prosthetic foot assembly also includes a support spring 400 coupled to the adapter and foot to limit the range of motion of the adapter and ankle in use and to provide improved energy storage and return. The adapter's range of motion depends at least in part on the stiffness of the support spring, which in turn depends at least in part on the position of the instantaneous center of rotation of the foot relative to the spring. For example, if the center of rotation 10 is located above a connection point 410 where the spring 400 is coupled to the foot member 110 as shown in FIG. 14A, the arc of the foot's travel path is to the left and right of the spring 400 and the spring 400 experiences little compression and/or extension. However, if the center of rotation 10 is more to the side of or perpendicular to the spring 400 as shown in FIG. 14B, the arc through which the foot travels is more aligned with the spring 400 and the spring 400 experiences greater compression and/or extension.

Figure 1C:
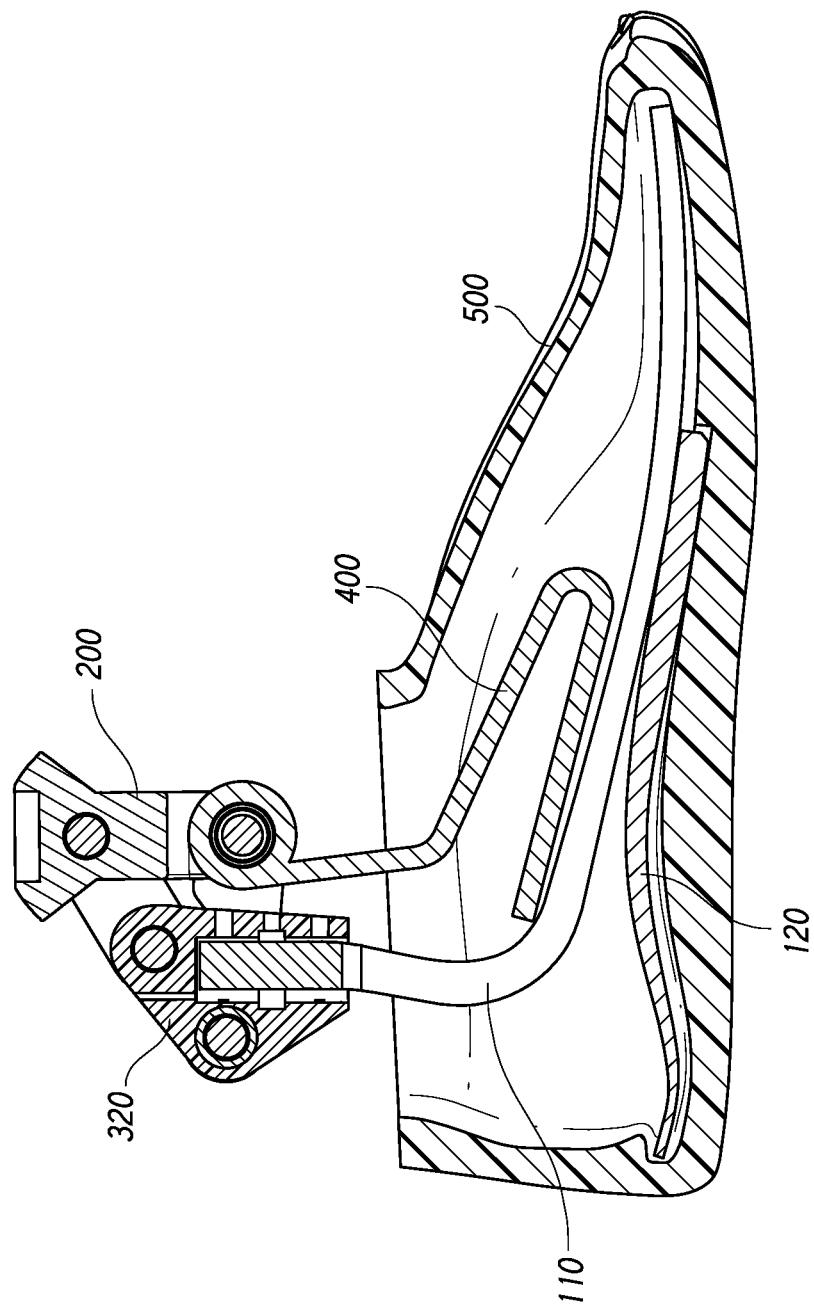

The support spring can be provided in various configurations to provide different functions and advantages. For example, the inverted orientation of the support spring 400 illustrated in FIG. 1A advantageously allows the adapter to be moved closer to the foot plate and allows the prosthetic foot to more easily fit within a cosmesis cover 500 as shown in FIGS. 1B and 1C compared to a support spring 400 having an orientation similar to that shown in the embodiments of, for example, FIGS. 4A-4D, the center embodiment of 4F, and the middle embodiment of 4H. As shown in FIG. 2K, the support spring 400 includes an aperture 430. To assemble the prosthetic foot with the support spring 400, the aperture 430 is aligned with an aperture 230 in the adapter 200 and coupled to the adapter 200 via a pin 350 and associated components as described herein. As shown in FIG. 2L, foam 420 can couple the support spring 400 to the foot member 110. In some embodiments, the prosthetic foot can also include a secondary support spring, for example, secondary support spring 362 shown in the example embodiment 100C of FIG. 4C. The secondary support spring 362 can help inhibit excessive motion of the adapter during use. As shown, a distal end of the secondary support spring 362 can be coupled to the foot member, for example, via bolts, fasteners, an adhesive, or any other appropriate means, and a proximal end of the secondary support spring 362 can be free, or unattached, and suspended beneath the adapter.

Figure 19A:
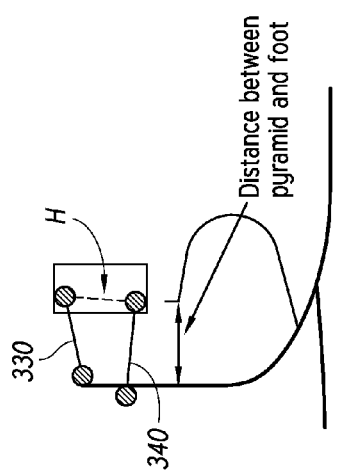
FIGS. 19A-19C schematically illustrate an example embodiment of a prosthetic foot assembly.
Figure 19B:
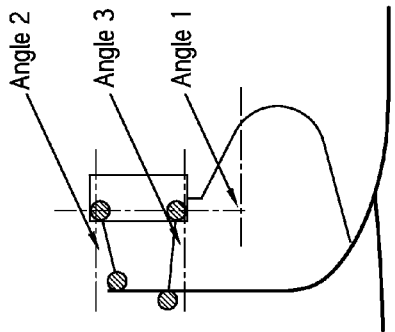
Figure 19C:
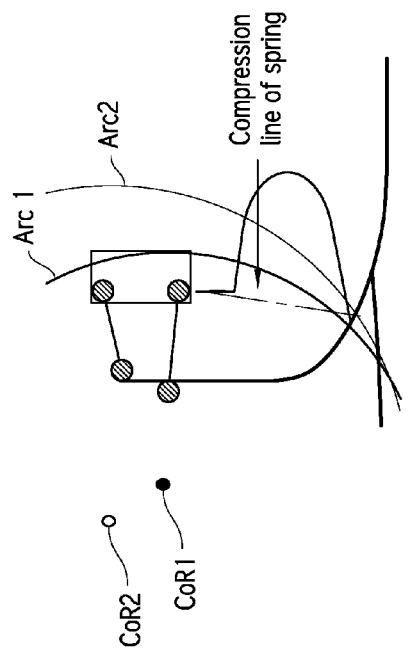

FIGS. 19A and 19B illustrate a schematic of one embodiment of a prosthetic foot assembly that provides beneficial features. In the illustration embodiment, the adapter 200 can have a length or height H of about 35 mm-36 mm, the top links 330 can have a length of about 30 mm-31 mm, and the bottom links 340 can have a length of about 46 mm-47 mm. Angle 1 can be about 90°, angle 2 can be about 30°, and angle 3 can be about 5°. This particular arrangement can allow for rotation of the foot 100 about the adapter 200 of up to about 15° and a vertical displacement of up to about 13 mm. FIG. 19C illustrates how a change in the center of rotation of the foot due to progression through the gait cycle affects the compression of the support spring 400. The center of rotation begins at position CoR1 and the spring 400 compresses along arc 1. As the foot progresses through the gait cycle, the center of rotation shifts to position CoR2, and the spring 400 compresses along arc 2. Arc 2 results in less compression of the spring 400. Of course, these dimensions and angles are exemplary dimensions and angles for one embodiment, and other configurations, dimensions, and angles are also possible.

Figure 15B:
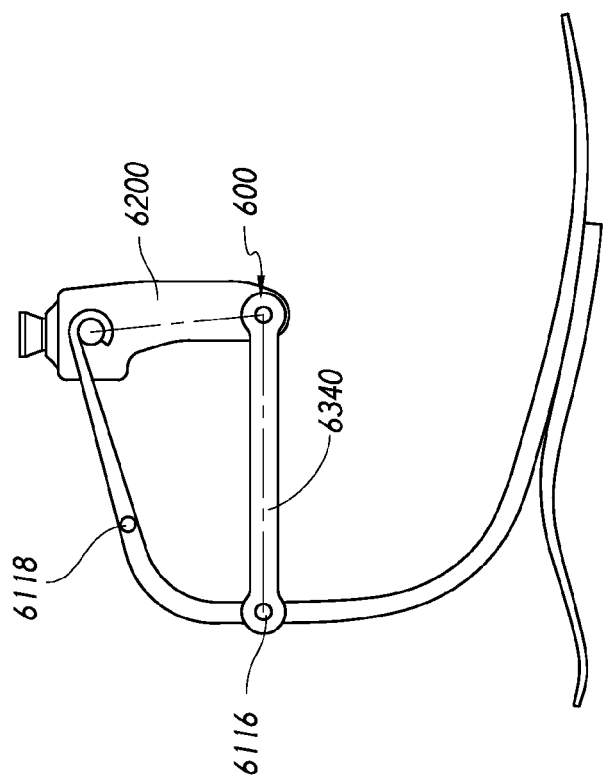
FIGS. 15A-16B schematically illustrate linkage assemblies formed by a foot and/or heel member.
Figure 15A:
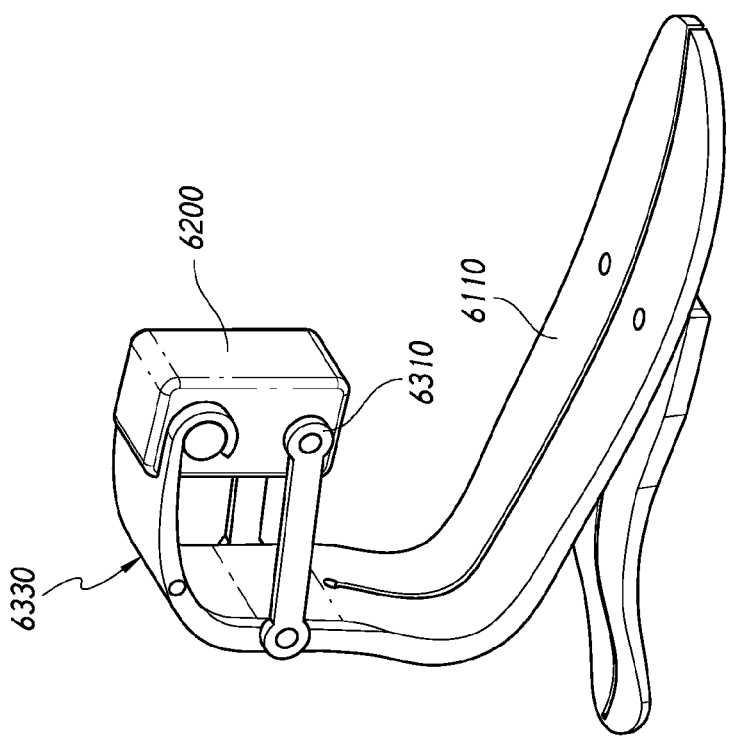

In some embodiments, torsion bars, torsion springs, compression springs, actuated springs, elastic elements, and/or other structures can be used as alternatives to a leaf spring to provide the functions of the support spring. In the example embodiment shown in FIGS. 15A and 15B, the adapter 6200 includes a torsion bar 600 that provides for energy storage and return. In the illustrated embodiment, the proximal portion of the foot member 6110 forms the top link 6330 and is coupled to the adapter 6200. The foot member 6110 can include a hinge 6118 to allow a portion of the foot member 6110 to function as the top link. In some embodiments, the hinge 6118 is in line with or centered in the foot member 6110. For example, the hinge 6118 can be formed as a pivot point, for example as shown in the example embodiment of FIG. 17A and discussed below, or with interlocking members that form a hinge, for example, as shown in the example embodiment of FIG. 17B and discussed below. In some embodiments, the hinge 6118 can be formed as one or more grooves that extend partially through a thickness of the foot member 6110 from either a top or a bottom surface of the foot member 6110 and/or one or more apertures in the foot member. Additional information regarding grooves and/or apertures that can act as hinges can be found in U.S. Patent Publication No. 2011/0208323, the entirety of which is hereby incorporated by reference herein and should be considered a part of this specification. Other types of hinges are also possible. The bottom link 6340 is coupled to the foot member 6110 via a hinge or joint 6116. As shown, the torsion bar 600 can be positioned at the joint 6310 where the bottom link 6340 is coupled to the adapter 6200. In some embodiments, the torsion bar 600 is designed to be able to withstand twisting of up to 10° and a moment of up to 450 Nm in use. In some embodiments, the torsion bar 600 can be made of a glass fiber, though other suitable materials can be used. Whereas a support spring generally limits the vertical displacement of the adapter during ambulation, the torsion bar 600 functions by limiting the angular range of the links during ambulation.

Figure 16B:
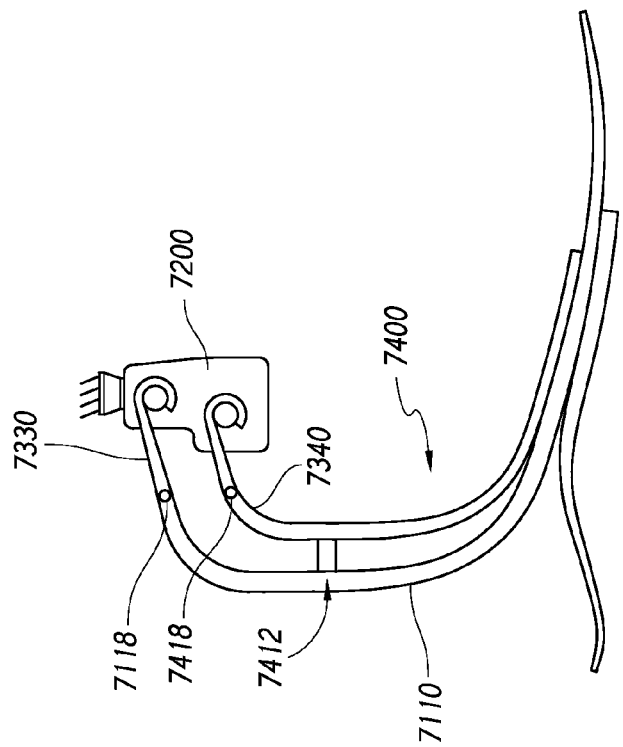
Figure 16A:
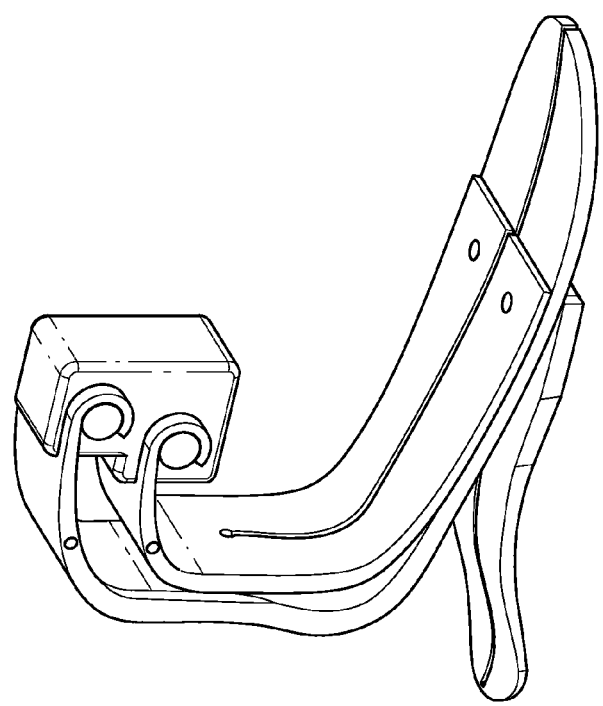

In some embodiments, the support spring can be shaped to form part of the linkage assembly. For example, in the embodiment shown in FIGS. 16A and 16B, the proximal portion of the foot member 7110 extends to the adapter 7200 to form the top link 7330, and a proximal portion of the support spring 7400 extends to the adapter 7200 to form the bottom link 7340. The foot member 7110 and support spring 7400 can include hinge points 7118, 7418 to allow portions of the foot member 7110 and support spring 7400 to function as links. Hinge points 7118, 7418 can include pivot points and/or interlocking members within the foot member 7110 and/or support spring 7400 and/or grooves extending partially through a thickness of the foot member 7110 and/or support spring 7400, for example, as discussed above with respect to FIG. 16B and below with respect to FIGS. 17A and 17B. In some embodiments, the support spring 7400 is coupled to the foot member 7110 at a hinge or joint 7412. This embodiment can also allow for a more robust as there are no separate links and fewer components that may fail.

Additional Features and Functions

Figure 17A:
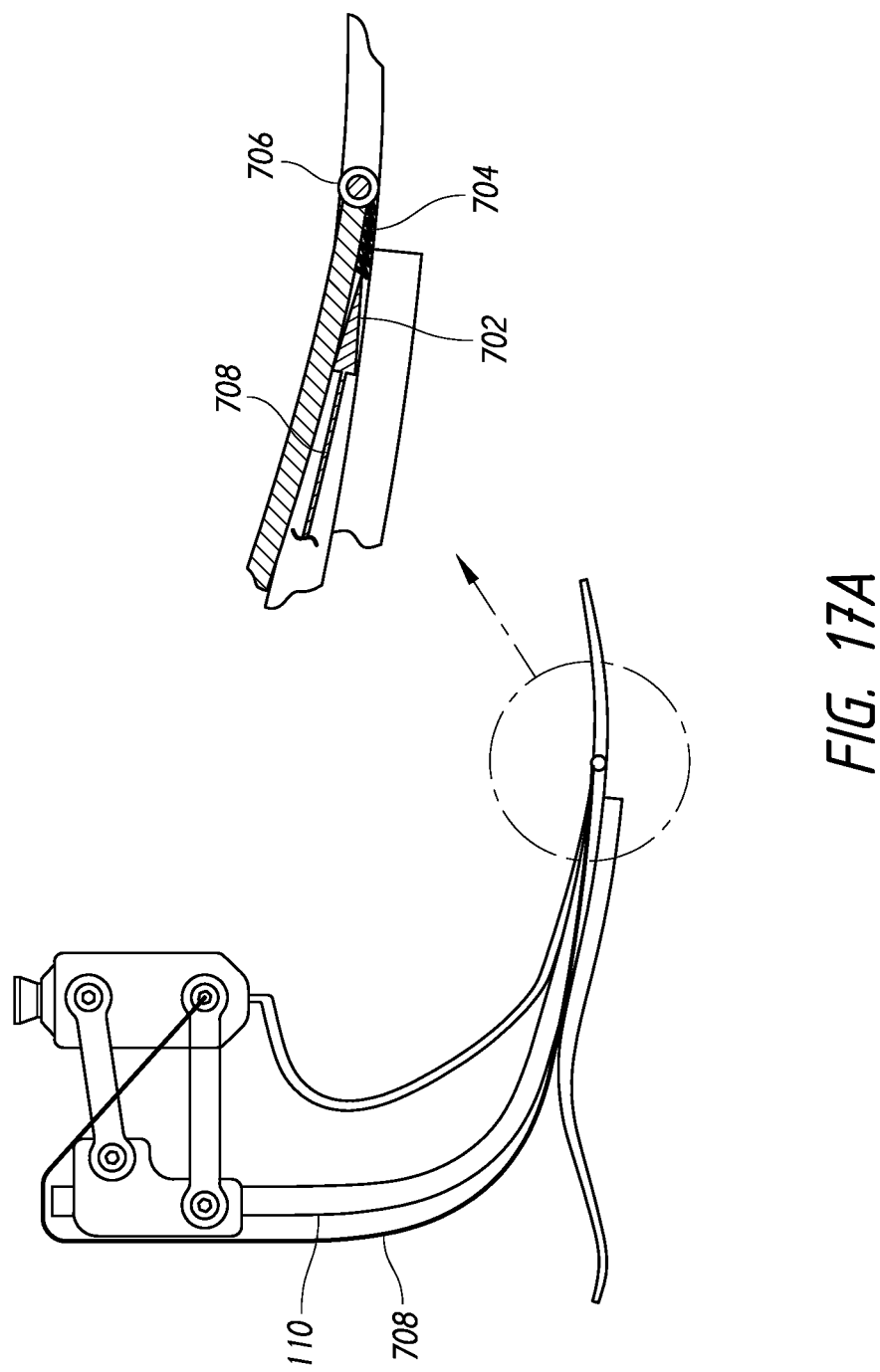
FIGS. 17A and 17B schematically illustrate prosthetic feet assemblies having mechanisms to provide toe clearance during swing.
Figure 17B:
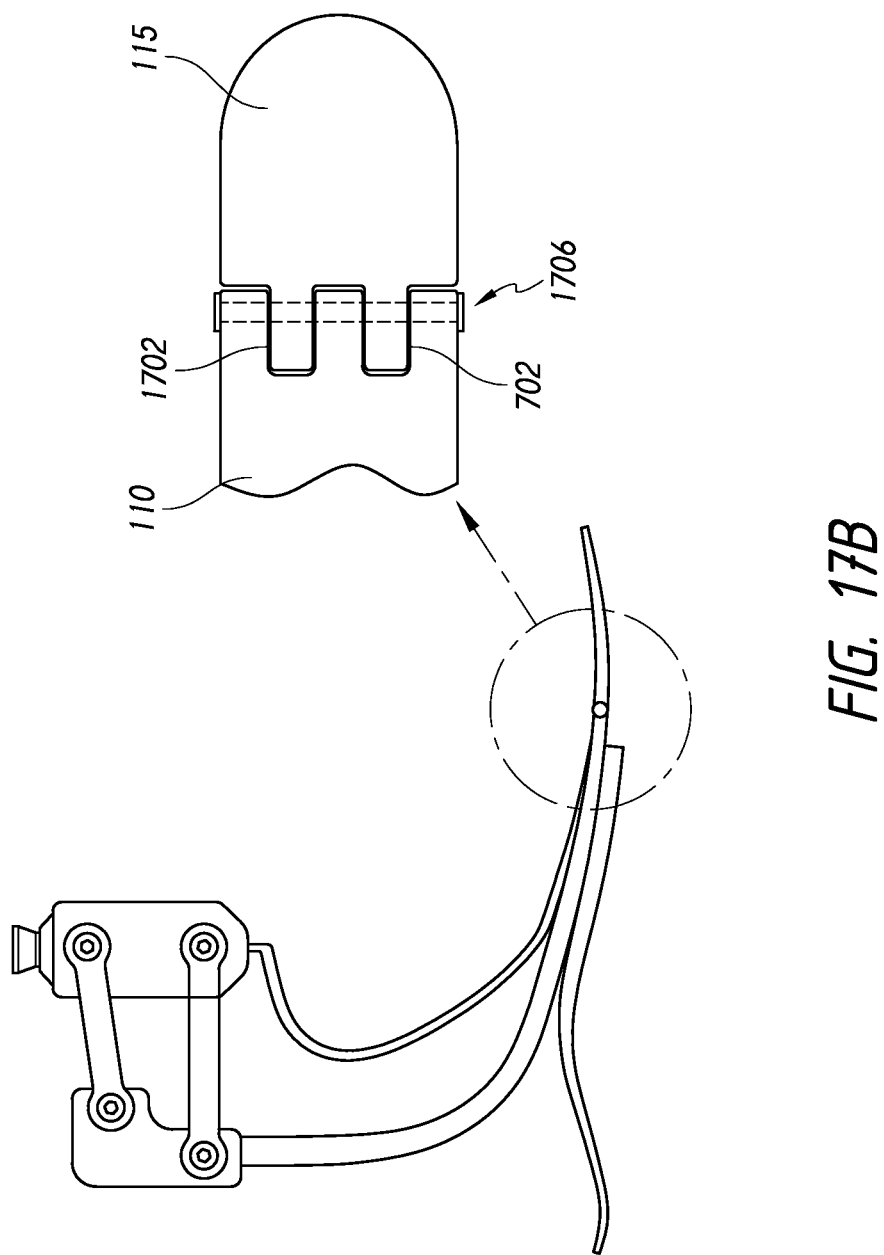

In some embodiments, the prosthetic foot assembly can include additional features to provide functions such as toe clearance and/or heel height adjustment. FIG. 17A illustrates an example embodiment of one mechanism for providing toe clearance during swing phase. The mechanism includes a wedge 702, spring 704, hinge 706 in the foot member 110, and wire 708. The hinge 706 creates a toe portion distal to the hinge 706 that is moveable relative to the rest of the foot member 110. When the foot is unloaded, the spring 704 pulls the wedge 702 against the toe portion, holding the toe portion in a lifted configuration and providing for improved toe clearance during swing. The wire 708 is coupled to the link assembly at one end and the wedge 702 at the other end. When the link assembly is loaded, the wire 708 is pulled toward the link assembly, thereby pulling the wedge away from the toe portion, as shown in the detail view of FIG. 17A, and allowing the foot member 110 to resume its natural shape. FIG. 17B illustrates an example embodiment of another mechanism for providing toe clearance during swing. As shown, a toe portion 115 is connected to the rest of the foot member 110 via a hinge 1706. Flexible bumpers 1702 are disposed in the hinge 1706 between the toe portion 115 and foot member 110. When the foot is unloaded, the bumpers 1702 cause the toe portion 115 to be lifted at an angle relative to the foot member 110.

Figure 18B:
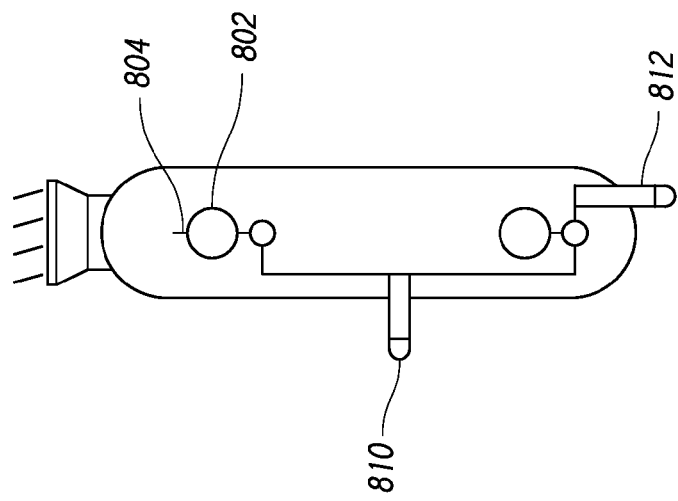
FIGS. 18A and 18B illustrate adapters allowing for heel height and/or leg length adjustment.
Figure 18A:
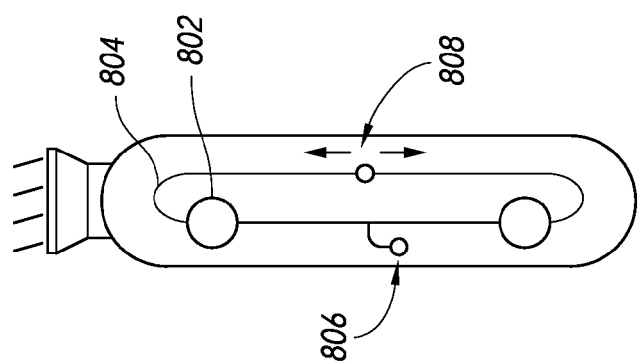

In some embodiments, the adapter 200 allows for adjustment of the heel height and/or leg length. FIG. 18A illustrates an example embodiment of a hydraulic system including two pin fixtures 802 and a motion rail 804. One pin fixture 802 can be moved up and down in the motion rail 804 via adjuster 806 to adjust the heel height. Both pin fixtures 802 can be moved in the motion rail 804 via adjuster 808 to adjust the leg length. FIG. 18B illustrates an example embodiment of a system for adjusting heel height and/or leg length using screws rather than a hydraulic mechanism. The heel height screw 812 moves one pin fixture to adjust the heel height, and the leg length screw 810 moves both pin fixtures to adjust the leg length.

Linkage Assembly for Knee Flexion

In some embodiments, a prosthetic foot includes a linkage assembly designed to simulate near-natural knee flexion, for example, early knee flexion during the stance phase of the gait cycle. The linkage assembly can advantageously help compensate for partial natural knee function that may be lost as a result of trans-tibial amputation, particularly when the user has a short residual limb or the residual limb is otherwise not able to withstand high moment loads. Natural knee flexion in early stance varies depending on an individual's walking style, age, and other factors; however, a natural knee often flexes by about 5° to about 15° in early stance. A trans-tibial amputee typically flexes his or her knee less than an able-bodied person, and in some cases, an amputee's knee may not flex at all if kept in a hyperextended state throughout stance. Normal early stance knee flexion provides for a quick and efficient anterior transition of the person's center of mass, and loss of this function in amputees can result in high loads and/or a reduced step length.

Figure 21B:
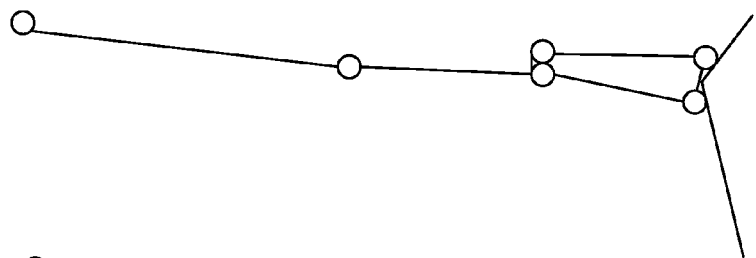
FIG. 21B schematically illustrates the linkage assembly of FIG. 21A during full stance.
Figure 21A:
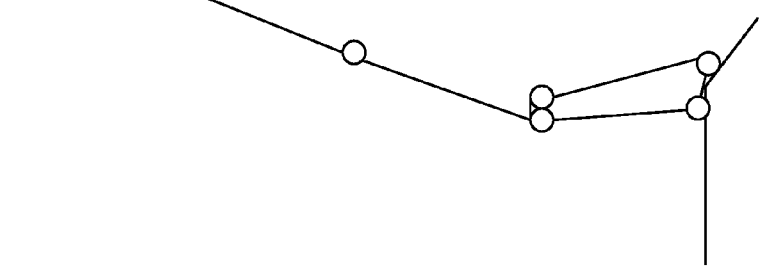
FIG. 21A schematically illustrates a schematic of a linkage assembly for simulating knee flexion during early stance.
Figure 20:
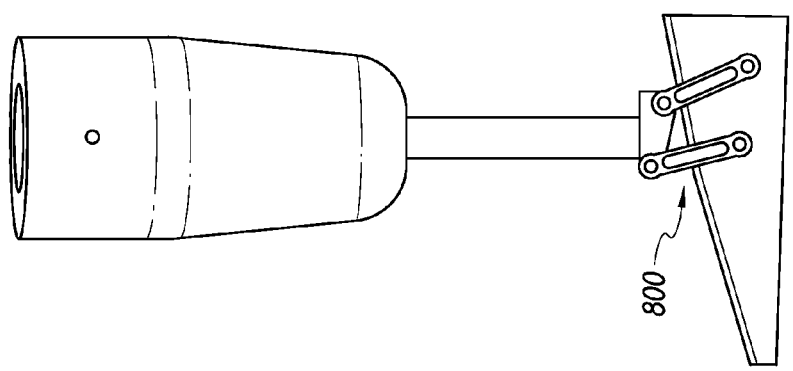
FIG. 20 schematically illustrates an example embodiment of a prosthetic foot and linkage assembly for simulating knee flexion.

A prosthetic foot according to some embodiments of the present disclosure includes a linkage assembly 800 positioned between a foot module and an ankle module that is configured to be attached to a pylon, for example as shown in FIG. 20. The links are arranged so as to buckle forward and provide a rearward angulation of the foot during early stance as shown in FIG. 21A to simulate natural knee flexion. In some embodiments, the foot includes a spring element designed to return the pylon to a neutral orientation so that there is substantially no angulation in the prosthesis during full stance, for example, as shown in FIG. 21B.

The linkage assembly for early stance knee flexion can also be used in combination with a prosthetic knee for trans-femoral amputees. This combination can also be beneficial as many prosthetic knees lack the ability to dynamically flex in early stance on their own. In some embodiments, the foot and linkage assembly can be designed to guide rotational or other movements during the gait cycle. In some embodiments, the foot and/or linkage assembly include spring and/or other dampening elements (e.g., hydraulic, friction, or other mechanisms) to help control the motion of the prosthesis.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above.

What is claimed is:

1. A prosthetic foot assembly, comprising:
   an elongate foot member extending from a generally vertical attachment portion at a proximal end to a distal end;
   an adapter configured to be coupled to a socket or pylon, wherein the adapter is horizontally spaced from and positioned in front of the vertical attachment portion of the foot member along a horizontal axis parallel to a support surface, the horizontal axis intersecting the adapter and vertical attachment portion when the foot assembly is resting on the support surface in a neutral position; and
   an ankle module comprising a connection sleeve coupled to the vertical attachment portion of the foot member, wherein a central vertical axis extending through the connection sleeve and vertical attachment portion of the foot member is horizontally spaced from a central vertical axis extending through the adapter when the foot assembly is resting on the support surface in the neutral position, the ankle module coupling the vertical attachment portion of the foot member to the adapter via four joints on the ankle module, wherein two of the four joints are on a medial side of the ankle module and two of the four joints are on a lateral side of the ankle module;
   wherein the ankle module allows translational and/or pivotal movement of the foot member relative to the adapter via the four joints.

2. The prosthetic foot assembly of claim 1, wherein the four joints comprise pivot points that allow pivotal movement of the foot member relative to the adapter via rotation about the pivot points.

3. The prosthetic foot assembly of claim 1, wherein the ankle module comprises one or more connection members extending between the joints of the ankle module.

4. The prosthetic foot assembly of claim 3, wherein the connection members comprise two top links and two bottom links, and the top and bottom links are not parallel to one another.

5. The prosthetic foot assembly of claim 3, wherein the connection members comprise two top links and two bottom links, and a length of the top links is not equal to a length of the bottom links.

6. The prosthetic foot assembly of claim 1, further comprising a support spring coupled to the adapter and foot member.

7. The prosthetic foot assembly of claim 1, wherein the connection sleeve comprises a recess configured to receive the vertical attachment portion of the foot member.

8. A prosthetic foot assembly, comprising:
   an adapter configured to be coupled to a socket or pylon, the adapter having four joints;
   an elongate foot member extending from a generally vertical attachment portion at a proximal end, the attachment portion of the foot member horizontally spaced from and positioned behind the adapter and having four joints along a horizontal axis parallel to a support surface, the horizontal axis intersecting the adapter and vertical attachment portion when the foot assembly is resting on the support surface in a neutral position; and
   a linkage assembly coupling and allowing relative movement between the foot member and the adapter, the linkage assembly comprising:
      an upper link and a lower link on both a medial and a lateral side of the foot member and adapter, the links extending between joints of the adapter and joints of the foot member;
      wherein the upper links have different lengths than the lower links and the upper links are not parallel to the lower links.

9. The prosthetic foot assembly of claim 8, further comprising a leaf spring coupled to the adapter and the foot member, the leaf spring configured to limit a range of motion of the adapter in use.

10. The prosthetic foot assembly of claim 8, further comprising a connection sleeve coupled to the attachment portion, wherein a vertical axis extending through the connection sleeve and attachment portion is horizontally spaced from a vertical axis extending through the adapter when the foot assembly is resting on the support surface in the neutral position, and wherein the linkage assembly couples the adapter and the connection sleeve.

11. The prosthetic foot assembly of claim 8, wherein the adapter comprises a male pyramid adapter.

* * * * *